US010913984B2

(12) United States Patent
Jamnikar et al.

(10) Patent No.: US 10,913,984 B2
(45) Date of Patent: Feb. 9, 2021

(54) PREDICTING GENETICALLY STABLE RECOMBINANT PROTEIN PRODUCTION IN EARLY CELL LINE DEVELOPMENT

(71) Applicant: Lek Pharmaceuticals d.d., Ljubljana (SI)

(72) Inventors: Uroš Jamnikar, Menges (SI); Kristina Gruden, Ljubljana (SI)

(73) Assignee: Lek Pharmaceuticals d.d., Ljubljana (SI)

( * ) Notice: Subject to any disclaimer, the term of this patent is extended or adjusted under 35 U.S.C. 154(b) by 316 days.

(21) Appl. No.: 15/525,315

(22) PCT Filed: Nov. 12, 2015

(86) PCT No.: PCT/EP2015/076390
§ 371 (c)(1),
(2) Date: May 9, 2017

(87) PCT Pub. No.: WO2016/075216
PCT Pub. Date: May 19, 2016

(65) Prior Publication Data
US 2017/0314082 A1 Nov. 2, 2017

(30) Foreign Application Priority Data

Nov. 12, 2014 (EP) ..................................... 14192809

(51) Int. Cl.
*C12Q 1/6888* (2018.01)
*G01N 33/50* (2006.01)
*C12N 5/073* (2010.01)

(52) U.S. Cl.
CPC ......... *C12Q 1/6888* (2013.01); *C12N 5/0603* (2013.01); *G01N 33/5023* (2013.01); *C12N 2510/02* (2013.01); *C12Q 2600/158* (2013.01); *G01N 2333/71* (2013.01); *G01N 2333/90666* (2013.01)

(58) Field of Classification Search
None
See application file for complete search history.

(56) References Cited

U.S. PATENT DOCUMENTS

2008/0070268 A1   3/2008   Anderson et al.
2014/0242692 A1*  8/2014   Rubin ................ A61K 31/7088
                                                           435/348

FOREIGN PATENT DOCUMENTS

WO    9921976       5/1999
WO    2006014899 A2 2/2006
WO    2008024459 A2 2/2008
WO    2008157299 A2 12/2008
WO    2010007388 A2 1/2010
WO    2010130800 A1 11/2010

OTHER PUBLICATIONS

Jamnikar et al. Transcriptome study and identification of potential marker genes related to stable expression of recombinant proteins in CHO clones. Oct. 2015. BMC Biotechnology. vol. 15, No. 98, 10 pages. (Year: 2015).*
Jiang et al. Regulation of Recombinant Monoclonal Antibody Production in Chinese Hamster Ovary Cells: A Comparative Study of Gene Copy Number, mRNA Level, and Protein Expression. Published on Web Nov. 15, 2005. Biotechnology Progress. vol. 22, pp. 313-318. (Year: 2005).*
International Search Report and Written Opinion for PCT/EP2015/076390, 18 pages.
Wu, Rick Sai-Chuen, et al., Etomidate Induces Cyotoxic Effects and Gene Expression in a Murine Leukemia Macrophage Cell Line, Anticancer Research, 2011, pp. 2203-2208.
Chusainow, Janet, et al., A Study of Monoclonal Antibody-Producing CHO Cell Lines: What Makes a Stable High Producer?, Biotechnology and Bioengineering, Wiley Interscience, Oct. 8, 2008.
Dorai, Haimanti, et al., Early Prediction of Instability of Chinese Hamster Ovary Cell Lines Expressing Recombinant Antibodies and Antibody-Fusion Proteins, Biotechnology and Bioengineering, Wiley Interscience, Nov. 8, 2011.
Kim, No Soo, Clonal Variability Within Dihydrofolate Reductase-Mediated Gene Amplified Chinese Hamster Ovary Cells: Stability in the Absence of Selective Pressure, Korea Advanced Institute of Science, Jun. 3, 1998.
Kim, Sang Jick, et al., Cytogenetic Analysis of Chimeric Antibody-Producing CHO Cells in the Course of Dihydrofolate Reductase-Mediated Gene Amplification and Their Stability in the Absence of Selective Pressure, Korea Advanced Institute of Science, Feb. 7, 1999.
Pfaffl, Michael W., A new mathematical model for relative quantification in real-time RT-PCR, Nucleic Acids Research, 2001, vol. 29, No. 9.
Vandesompele, Jo, et al., Accurate normalization of real-time quantitative RT-PCR data by geometric averaging of multiple internal control genes, Genome Biology, 2002, 3, Jun. 18, 2002.

* cited by examiner

*Primary Examiner* — Channing S Mahatan
(74) *Attorney, Agent, or Firm* — Luedeka Neely Group, P.C.

(57) ABSTRACT

The present invention relates in general to the field of recombinant protein expression. In particular, the present invention relates to a method for selecting a suitable candidate cell clone for recombinant protein expression and to a host cell for recombinant protein expression, the host cell exhibiting artificially modified gene expression of at least one gene selected from the group consisting of: Hist1h2bc, Egrl, BX842664.2/Hist 1h3c, Dhfr, Fgfr2, AC115880.11, Mmp10, Vsnll (optional), CU459186.17, El 30203 B14Rik, Cspg4, C1qtnfl, Foxp2, and Ptpre.

14 Claims, 9 Drawing Sheets

Specification includes a Sequence Listing.

SEQUENCE LISTING

```
<160> NUMBER OF SEQ ID NOS: 42

<210> SEQ ID NO 1
<211> LENGTH: 23
<212> TYPE: DNA
<213> ORGANISM: Cricetulus griseus

<400> SEQUENCE: 1
gcctgagtta cacatccatc aca                                          23

<210> SEQ ID NO 2
<211> LENGTH: 18
<212> TYPE: DNA
<213> ORGANISM: Cricetulus griseus

<400> SEQUENCE: 2
ggcccagaca tggacact                                                18

<210> SEQ ID NO 3
<211> LENGTH: 27
```

```
<212> TYPE: DNA
<213> ORGANISM: Cricetulus griseus

<400> SEQUENCE: 3
cgagcttttc accagtagag atagtta                                      27

<210> SEQ ID NO 4
<211> LENGTH: 24
<212> TYPE: DNA
<213> ORGANISM: Cricetulus griseus

<400> SEQUENCE: 4
ccagtgggta catcacatga gaga                                         24

<210> SEQ ID NO 5
<211> LENGTH: 21
<212> TYPE: DNA
<213> ORGANISM: Cricetulus griseus

<400> SEQUENCE: 5
atatggggat tggcaagaac g                                            21

<210> SEQ ID NO 6
<211> LENGTH: 23
<212> TYPE: DNA
<213> ORGANISM: Cricetulus griseus

<400> SEQUENCE: 6
acgaggagta gacctgatga tgt                                          23

<210> SEQ ID NO 7
<211> LENGTH: 20
<212> TYPE: DNA
<213> ORGANISM: Cricetulus griseus

<400> SEQUENCE: 7
gccatgtggc ctagcttcat                                              20

<210> SEQ ID NO 8
<211> LENGTH: 22
<212> TYPE: DNA
<213> ORGANISM: Cricetulus griseus

<400> SEQUENCE: 8
cattccacag acactggatg ga                                           22

<210> SEQ ID NO 9
<211> LENGTH: 25
<212> TYPE: DNA
<213> ORGANISM: Cricetulus griseus

<400> SEQUENCE: 9
gggcttacgg cttatactct atgtg                                        25

<210> SEQ ID NO 10
<211> LENGTH: 24
<212> TYPE: DNA
<213> ORGANISM: Cricetulus griseus

<400> SEQUENCE: 10
caggaatcga gccacaaatt gatg                                         24

<210> SEQ ID NO 11
```

```
<211> LENGTH: 29
<212> TYPE: DNA
<213> ORGANISM: Cricetulus griseus

<400> SEQUENCE: 11
acccttaagc atatgtcttt ggaatttga                                        29

<210> SEQ ID NO 12
<211> LENGTH: 16
<212> TYPE: DNA
<213> ORGANISM: Cricetulus griseus

<400> SEQUENCE: 12
gggaggccgg ttttgg                                                      16

<210> SEQ ID NO 13
<211> LENGTH: 21
<212> TYPE: DNA
<213> ORGANISM: Cricetulus griseus

<400> SEQUENCE: 13
gctcacctct ggccttaaag g                                                21

<210> SEQ ID NO 14
<211> LENGTH: 22
<212> TYPE: DNA
<213> ORGANISM: Cricetulus griseus

<400> SEQUENCE: 14
ccctccagtc tcttggctaa tg                                               22

<210> SEQ ID NO 15
<211> LENGTH: 25
<212> TYPE: DNA
<213> ORGANISM: Cricetulus griseus

<400> SEQUENCE: 15
gatgatgaag gtcctgaagc tgtta                                            25

<210> SEQ ID NO 16
<211> LENGTH: 20
<212> TYPE: DNA
<213> ORGANISM: Cricetulus griseus

<400> SEQUENCE: 16
ccatgaggca ctgggacttt                                                  20

<210> SEQ ID NO 17
<211> LENGTH: 24
<212> TYPE: DNA
<213> ORGANISM: Cricetulus griseus

<400> SEQUENCE: 17
ttgacacata cagctccaat tcca                                             24

<210> SEQ ID NO 18
<211> LENGTH: 18
<212> TYPE: DNA
<213> ORGANISM: Cricetulus griseus

<400> SEQUENCE: 18
cccgagtggg agctgact                                                    18
```

```
<210> SEQ ID NO 19
<211> LENGTH: 27
<212> TYPE: DNA
<213> ORGANISM: Cricetulus griseus

<400> SEQUENCE: 19
cattctttgg aagtacttga actcgtt                                    27

<210> SEQ ID NO 20
<211> LENGTH: 29
<212> TYPE: DNA
<213> ORGANISM: Cricetulus griseus

<400> SEQUENCE: 20
gtatcaccta tttccattgt ctcaattgc                                  29

<210> SEQ ID NO 21
<211> LENGTH: 26
<212> TYPE: DNA
<213> ORGANISM: Cricetulus griseus

<400> SEQUENCE: 21
aaacaggtga aatagagga ctttgg                                      26

<210> SEQ ID NO 22
<211> LENGTH: 20
<212> TYPE: DNA
<213> ORGANISM: Cricetulus griseus

<400> SEQUENCE: 22
gccaaagaag ccaggactga                                            20

<210> SEQ ID NO 23
<211> LENGTH: 31
<212> TYPE: DNA
<213> ORGANISM: Cricetulus griseus

<400> SEQUENCE: 23
cccagttagt ggtaattcta tcaagtactt t                               31

<210> SEQ ID NO 24
<211> LENGTH: 26
<212> TYPE: DNA
<213> ORGANISM: Cricetulus griseus

<400> SEQUENCE: 24
tcaaactgtg atgatccatg gaagaa                                     26

<210> SEQ ID NO 25
<211> LENGTH: 25
<212> TYPE: DNA
<213> ORGANISM: Cricetulus griseus

<400> SEQUENCE: 25
ttccgaaatg aacaaatcgt ctgtt                                      25

<210> SEQ ID NO 26
<211> LENGTH: 22
<212> TYPE: DNA
<213> ORGANISM: Cricetulus griseus

<400> SEQUENCE: 26
ttgtgcaaca cccagagact ac                                         22
```

```
<210> SEQ ID NO 27
<211> LENGTH: 20
<212> TYPE: DNA
<213> ORGANISM: Cricetulus griseus

<400> SEQUENCE: 27
cattctggag aaccaaagct                                               20

<210> SEQ ID NO 28
<211> LENGTH: 25
<212> TYPE: DNA
<213> ORGANISM: Cricetulus griseus

<400> SEQUENCE: 28
gcaaactgag tctctgtgtc ttagg                                         25

<210> SEQ ID NO 29
<211> LENGTH: 16
<212> TYPE: DNA
<213> ORGANISM: Cricetulus griseus

<400> SEQUENCE: 29
ttggcctcac atctcc                                                   16

<210> SEQ ID NO 30
<211> LENGTH: 15
<212> TYPE: DNA
<213> ORGANISM: Cricetulus griseus

<400> SEQUENCE: 30
aagcgcccca tcagc                                                    15

<210> SEQ ID NO 31
<211> LENGTH: 16
<212> TYPE: DNA
<213> ORGANISM: Cricetulus griseus

<400> SEQUENCE: 31
acgggcttca gtcttc                                                   16

<210> SEQ ID NO 32
<211> LENGTH: 16
<212> TYPE: DNA
<213> ORGANISM: Cricetulus griseus

<400> SEQUENCE: 32
aaactgtgcc aaactc                                                   16

<210> SEQ ID NO 33
<211> LENGTH: 16
<212> TYPE: DNA
<213> ORGANISM: Cricetulus griseus

<400> SEQUENCE: 33
agacctaccc tggcct                                                   16

<210> SEQ ID NO 34
<211> LENGTH: 17
<212> TYPE: DNA
<213> ORGANISM: Cricetulus griseus

<400> SEQUENCE: 34
cagtgctgga cgttgtt                                                  17
```

<210> SEQ ID NO 35
<211> LENGTH: 16
<212> TYPE: DNA
<213> ORGANISM: Cricetulus griseus

<400> SEQUENCE: 35
caagctcttg aattcc                                                  16

<210> SEQ ID NO 36
<211> LENGTH: 16
<212> TYPE: DNA
<213> ORGANISM: Cricetulus griseus

<400> SEQUENCE: 36
ctgaccccat catccc                                                  16

<210> SEQ ID NO 37
<211> LENGTH: 16
<212> TYPE: DNA
<213> ORGANISM: Cricetulus griseus

<400> SEQUENCE: 37
acggtgccat gaatcc                                                  16

<210> SEQ ID NO 38
<211> LENGTH: 16
<212> TYPE: DNA
<213> ORGANISM: Cricetulus griseus

<400> SEQUENCE: 38
aatgcctgca acaccg                                                  16

<210> SEQ ID NO 39
<211> LENGTH: 16
<212> TYPE: DNA
<213> ORGANISM: Cricetulus griseus

<400> SEQUENCE: 39
tcatccagcc cctccc                                                  16

<210> SEQ ID NO 40
<211> LENGTH: 16
<212> TYPE: DNA
<213> ORGANISM: Cricetulus griseus

<400> SEQUENCE: 40
ttgctgcccg gtatcc                                                  16

<210> SEQ ID NO 41
<211> LENGTH: 16
<212> TYPE: DNA
<213> ORGANISM: Cricetulus griseus

<400> SEQUENCE: 41
cagctcagcc ctcttc                                                  16

<210> SEQ ID NO 42
<211> LENGTH: 16

```
<212> TYPE: DNA
<213> ORGANISM: Cricetulus griseus

<400> SEQUENCE: 42
ccacaaccaa attcag                                                    16
```

PREDICTING GENETICALLY STABLE RECOMBINANT PROTEIN PRODUCTION IN EARLY CELL LINE DEVELOPMENT

This application is a Section 371 national phase entry of PCT application PCT/EP2015/076390, filed Nov. 12, 2015. This application also claims the benefit of the earlier filing date of European patent application 14192809.3, filed Nov. 12, 2014.

This application contains a Sequence Listing which has been submitted electronically in ASCII format and is herein incorporated by reference. The ASCII file, created on Mar. 13, 2017, is named 72599us-temp-20170313-HEX-006 PCT_ST25, and is 6,754 bytes in size.

The present invention relates in general to the field of recombinant protein production. In particular, the present invention relates to a method for selecting a suitable candidate cell clone for recombinant protein production and to a host cell for recombinant protein production, the host cell exhibiting artificially modified gene expression of at least one gene selected from the group consisting of: Hist1h2bc, Egr1, Bx842664.2/Hist1h3c, Dhfr, Fgfr2, AC115880.11, Mmp10, Vsnl1, CU459186.17, E130203B14Rik, Cspg4, C1qtnf1, Foxp2, and Ptpre.

Production of recombinant proteins has become an important factor in modern biotechnology. Chinese hamster ovary (CHO) cells have become in many cases the host of choice because of their capacity for proper protein folding, assembly, and posttranslational modification. Moreover CHO cell lines have been well characterized and their history of regulatory approval for recombinant proteins produced from these cell lines is very well known. The most widely used expression system for recombinant protein production is the gene amplification procedure, which uses the CHO-Dhfr expression system. Moreover, CHO cells, just like many other host cell systems, are known to have a very unstable karyotype due to chromosome rearrangements arising from translocations and homologous recombination. Unstable recombinant protein production has been observed in 8-63% of all recombinant CHO cell lines, using DHFR/GS expression systems, in the presence or absence of selection pressure. Unstable recombinant protein production in turn leads to a loss in recombinant protein productivity. The exact molecular mechanism causing unstable recombinant protein production is not fully understood. Thus, the conventional methodologies involve empirically testing cell lines for long-term stable recombinant protein production and consequently require culturing said cell lines over extended periods of time (up to several months) prior to actual selection of cell lines for production purposes.

Most publications in the art mainly focus on expression of the recombinant gene itself and its expression over time. Flow cytometry has also been used for identification of apoptotic cells which serve as a marker of unstable cells. For example, Dorai and colleagues have identified apoptosis as a possible cause of recombinant protein instability by using the flow cytometry method for identifying apoptotic cells (caspase 3 activity) in early cell line development. Examination by flow cytometry showed that caspase 3 and annexin V apoptotic markers could be used to identify cell lines with stable recombinant protein production (Dorai, H. et al., 2011, Biotechnol Bioeng, 109:1016-1030).

In general, previous publications identified that instability of recombinant protein production during long term cultivation could result from recombinant gene loss during long term cultivation, especially when selection pressure is not present (Kim N S et al., 1998, Biotechnol Bioeng 60:679-688, Kim S J et al., 1999, Biotechnol Bioeng 64:741-749; Chuisanow J et al., 2009, Biotechnol Bioeng 102:1182-1196).

However, there is still an immense need in the art for a means allowing identification of suitable, preferably long-term stable recombinant protein production, candidate cell clones early on in cell line development to avoid the need of long term cultivation and respective costs in terms of time and money.

Thus, the problem to be solved by the present invention was to provide a means allowing identification of suitable, preferably long-term stable, candidate cell clones early on in cell line development. The inventor has solved said problem by way of the subject-matter set forth in the appended claims.

In the following, a brief description of the appended figures will be given. The figures are intended to illustrate the present invention in more detail. However, they are not intended to limit the subject-matter of the invention to any extent.

FIG. 1: illustrates a general flowchart for the conducted study, where stable recombinant protein production was monitored in a 10-week long cultivation without and with selection pressure (MTX).

FIG. 2: gives examples for clones with stable and unstable recombinant protein production. The productivity at the end of stability study was compared to the productivity at the beginning and if productivity has not changed for more than 30%, the clones were marked as "stable", otherwise the clones were considered as being "unstable". A: Example for a clone with unstable protein production; B: Example for a clone with stable protein production.

FIG. 3 shows a correlation between the recombinant protein production and recombinant gene copy numbers in the samples. The productivity and recombinant gene copy numbers of the clones are represented according to the beginning and the end of the 10-week study, as indicated. A decline in the recombinant gene average copies by 44% (from 5.4 to 3 recombinant gene copies per cell) is observed for the stable clones, although their productivity declined by only 9% (7 to 6.4 arbitrary units). For the unstable clones, the recombinant gene copy numbers declined by 61% (from 5.4 to 2.1 recombinant gene copies per cell); furthermore, their productivity declined by 67% (from 7 to 2.3 arbitrary units). If productivity at the end of stability study, compared to the beginning of the study, has not change for more than 30% and if change in copy number in the same time period was below 50%, the clones were marked as "stable".

FIG. 4 shows the expression values ($\log_2$ FC) for 13 of the 14 genes analysed, presented in a Box whisker plot (BWP). BWP of the relative gene expression for the stable (S) versus unstable (US) clones. The normalised expression values ($\log_2$FC) for each gene are represented for all of the stable and unstable clones separately, as combined for all four of the time points ($P_{adj}$<0.05).

FIG. 5 is a three-dimensional representation based on discrimination analysis. The properties of the clones (originating from the beginning of the study) are described by the relative expression values of the three selected genes hDhfr (hamster Dhfr), Egr1 and Hist1h2bc, as indicated on the three axes. In the three-dimension representation, there is a clear separation of the clones with stable and unstable recombinant protein production.

FIG. 6 is a three-dimensional representation based on discrimination analysis where clones' (originating from the end of study) properties are described by the relative expression values of three genes hDhfr (hamster Dhfr), Egr1, Hist1h2bc. Each gene expression is presented on its own separate axis; hence, a three-dimensional representation of the clones was achieved. In the three-dimensional space a clear separation of stable and unstable clones was achieved.

Figure 1:
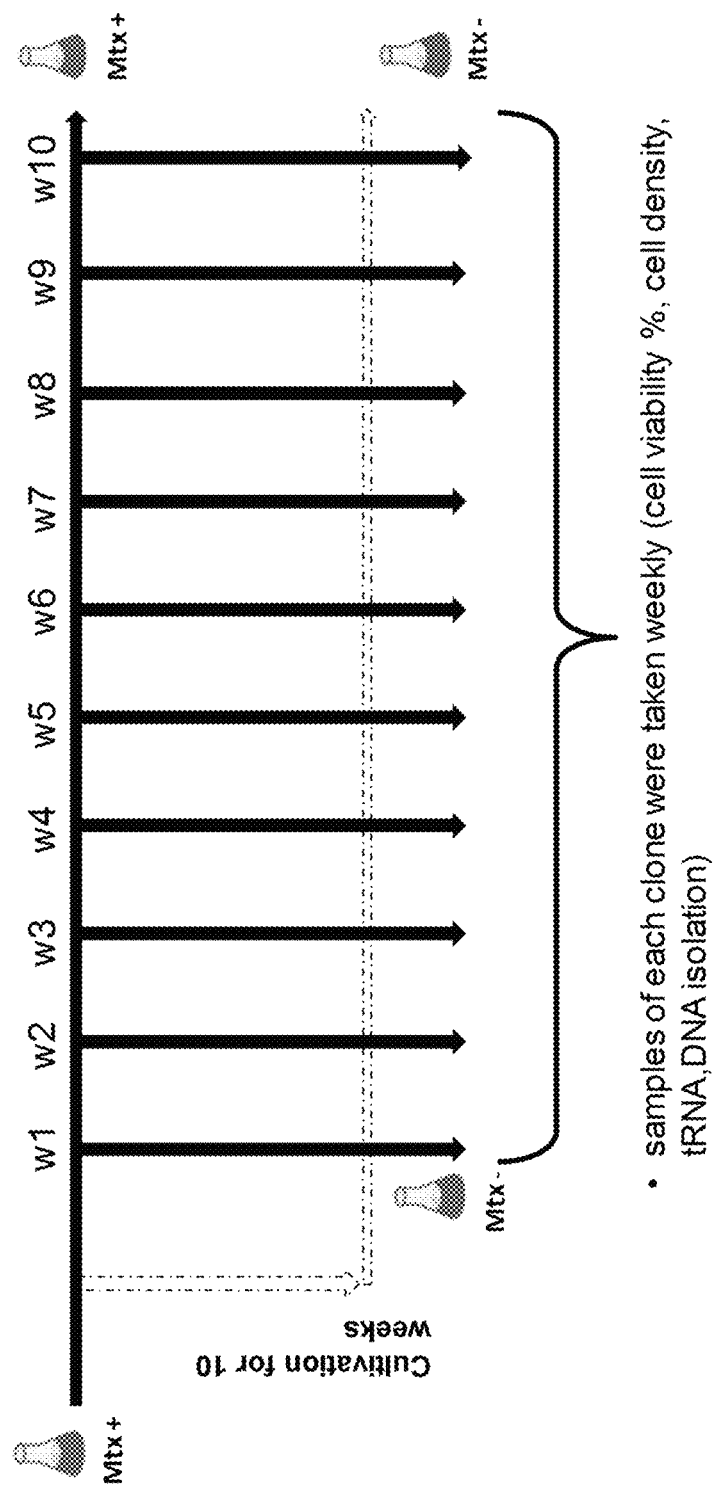

In a first aspect, the present invention relates to a method for selecting a suitable candidate cell clone for recombinant protein expression, the method comprising the steps of:
a) determining for at least two cell clones, preferably producing a recombinant protein, the expression level of a gene selected from the group consisting of:
Hist1h2bc, Egr1, BX842664.2/Hist1h3c, Dhfr, Fgfr2, AC115880.11, Mmp10, CU459186.17, E130203B14Rik, Cspg4, C1qtnf1, Foxp2, Vsnl1, and Ptpre.
b) selecting out of said at least two cell clones a cell clone for further expansion, whose expression level of said gene is with respect to the expression level of said same gene in at least one other clone tested in step a):
i) upregulated, if the gene is selected from the group of genes consisting of:
Hist1h2bc, BX842664.2/Hist1h3c, Dhfr, AC115880.11, Fgfr2, Mmp10, Vsnl1 and CU459186.17, or
ii) downregulated, if the gene is selected from the group of genes consisting of:
Egr1, E130203B14Rik, Cspg4, C1qtnf1, Foxp2, and Ptpre.

In a preferred embodiment, Vsnl1 is not among the genes for which the expression level is determined, i.e. in such embodiments the expression level of a gene selected from the group consisting of:
Hist1h2bc, Egr1, BX842664.2/Hist1h3c, Dhfr, Fgfr2, AC115880.11, Mmp10, CU459186.17, E130203B14Rik, Cspg4, C1qtnf1, Foxp2, and Ptpre
is determined. This is reflected in the following by the indication that Vsnl1 gene is optional, i.e. may or may not be in the group of genes mentioned.

The method according to the present invention allows a selection of a promising cell clone early on in cell line development without the need for long term cultivation and analysis. For this purpose the expression level of at least one gene selected from the group consisting of Hist1h2bc, Egr1, BX842664.2/Hist1h3c, Dhfr, Fgfr2, AC115880.11, Mmp10, CU459186.17, E130203B14Rik, Cspg4, C1qtnf1, Foxp2, Vsnl1 (optional), and Ptpre is determined in step a) of the inventive method. If herein reference is made to determining the "expression level", then in particular the expression level of RNA expression is contemplated. While protein expression may theoretically also be used, said approach will usually be much less efficient. A person skilled in the art is readily familiar with determining expression levels, in particular of RNA. For example, as small aliquot may be removed from the candidate clone sample and quantitative RT-PCR may be used for determination of the respective expression levels. Moreover, determining the "expression level" in the context of the inventive method refers to determining the "expression level" of the endogenous gene(s) only, and not to determining the "expression level" of the same genes if present as recombinant gene. For example, determining the expression level of Dhfr) means exclusively determining the expression level of the endogenous gene, e.g. hamster Dhfr (hDhfr), and not of Dhfr on a recombinant gene (recombinant Dhfr, rDhfr).

Step a) refers to the determination of the expression level in at least two cell clones. Two cell clones are the minimum requirement to allow any comparison in expression level. Already for two clones it will be possible to decide with the method of the present invention, which of the two clones will most likely be the more promising candidate for cell line development. However, usually many more clones will be analysed. For example, the method of the invention may involve determining said expression level for at least 3, 4, 5, 6, 7, 8, 9, 10, 15, 20, 50, 75 or at least 100 candidate clones.

The method of the present invention can be carried out prior to transfection, i.e. the cell clones need not yet express a recombinant gene (protein). In such scenario a pre-selection of a promising cell clone is already made by establishing clones of a given cell line and analysing them with the method of the invention. The selected clone or clones may then be used for transfection etc. Usually however, or even in addition, the expression level of the inventive group of genes is analysed after the host cell has been transfected or transformed and the respective culture has been plated to generate single cell clones. Then, the candidate clones express at least one recombinant protein. According to the invention, the type of recombinant protein expressed is not of relevance. It may be any type of recombinant protein. The recombinant protein may be for example an antibody, antibody light or heavy chain, a toxin, a cytokine, a growth factor, a growth factor receptor, an enzyme, or a hormone. Preferably, the recombinant protein is an antibody. As the type of recombinant protein expressed is not of particular relevance for the present invention, it is not a prerequisite, although preferred, that the clones (for which the expression level of a particular gene is determined in step a) of the inventive method) express the very same recombinant protein (see also further below). Ideally, they should however preferably at least express the same type of recombinant protein or a recombinant protein of comparable size. In a preferred embodiment of the invention the recombinant protein expressed by said clones is the same type of recombinant protein, such as an antibody.

The method of the present invention may be carried out by determining the expression level of only one gene selected from the group consisting of: Hist1h2bc, Egr1, BX842664.2/Hist1h3c, Dhfr, Fgfr2, AC115880.11, Mmp10, CU459186.17, E130203B14Rik, Cspg4, C1qtnf1, Foxp2, Vsnl1 (optional) and Ptpre. In particularly preferred embodiments, the expression level of at least one gene selected from the group consisting of Egr1, BX842664.2/Hist1h3c and Dhfr is determined. In other embodiments, the expression level of at least one gene selected from the group consisting of Fgfr2, BX842664.2/Hist1h3c, E130203b14Rik, Cspg4, Mmp10 (optional) and Ptpre, or from the group consisting of Fgfr2, BX842664.2/Hist1h3c, E130203b14Rik, Cspg4, and Ptpre is determined.

However, while the invention may be carried out by determining the expression level of only one gene selected from said group, analysis of more than one gene may prove helpful for the selection decision. Thus, in a preferred embodiment, the expression level of more than one gene selected from the group consisting of Hist1h2bc, Egr1, BX842664.2/Hist1h3c, Dhfr, Fgfr2, AC115880.11, Mmp10, CU459186.17, E130203B14Rik, Cspg4, C1qtnf1, Foxp2, Vsnl1 (optional) and Ptpre is determined. For example, an inventive method may involve determining the expression level of at least 2, at least 3, at least 4, at least 5, at least 6, at least 7, at least 8, at least 9, at least 10, at least 11, at least 12, at least 13 or all 14 genes of said group. It is particularly preferred if the expression level of at least three genes of said group are determined. More preferably, the expression level of at least three genes of said group are determined and the at least three genes encompass at least one gene selected from the group consisting of Egr1, Hist1h2bc and Dhfr or at least one gene selected from the group consisting of Fgfr2, BX842664.2/Hist1h3c, E130203b14Rik, Cspg4, Mmp10 and Ptpre or at least one gene selected from the group consisting of Fgfr2, BX842664.2/Hist1h3c, E130203b14Rik, Cspg4, and Ptpre. Even more preferably, the expression level of at least Egr1, Hist1h2bc and Dhfr is determined in step a) of the inventive method, or of at least three genes selected from the group consisting of Fgfr2, BX842664.2/Hist1h3c, E130203b14Rik, Cspg4, Mmp10 and Ptpre or at least three genes selected from the group consisting of Fgfr2, BX842664.2/Hist1h3c, E130203b14Rik, Cspg4, and Ptpre.

In most embodiments of the present invention the expression level will be determined in step a) of the inventive method in parallel. However, that need not necessarily be the case. For example, there may be a first round of cloning, in which at least one clone is analysed as required by step a). The expression levels determined for said clone (or clones) may then serve for later cloning experiments as reference (the reference clone has still been analysed as required by step a) of the inventive method, albeit at a different point in time). Thus, in some embodiments of the invention, the expression level for said gene or genes are not determined in parallel in step a) for said at least two cell clones. In particular, in such scenario it also becomes evident that the recombinant protein expressed by said at least two clones need not be identical (see above). For example, if in a first round of cloning a particular promising (or disappointing) clone for antibody A has been identified, the respective expression levels may serve as reference for later cloning experiments with clones for antibody B (see in this respect also further below the passage on selection of a candidate clone by indirect means). While the expression levels of the cell need not be determined in parallel, the conditions under which the expression levels are determined should of course be preferably identical. For example, step a) is preferably carried out after the same time span after cloning, e.g. within two weeks after cloning (e.g. in the time period of 48 hours to 14 days after cloning, 72 hours to 14 days after cloning, 48 hours to 10 days after cloning, 72 hours to 10 days after cloning, etc.), even more preferably within one week after cloning (e.g. in the time period of 48 hours to 7 days after cloning, 72 hours to 7 days after cloning, 48 hours to 4 days after cloning, 72 hours to 4 days after cloning, etc.). Furthermore, the expression level of said gene or genes is preferably determined for said at least two clones in early log phase (exponential phase) of growth. A person skilled in the art will be familiar with the respective cell culturing techniques and can ascertain said condition, e.g. by appropriate splitting of the cultures and replenishing of fresh media. General culture conditions should preferably be identical, except maybe for necessary deviations, e.g. with respect to antibiotic resistance selection, amplification with MTX etc. It is self-evident, that the cell background (e.g. CHO cell) of the clones analysed in step a) of the inventive method may not be different.

The method of the present invention is not limited to a particular type of host cell. Since instability and associated loss in productivity is frequently encountered, the method of the present invention may be applied in principle to any type of host cell. However, in a preferred embodiment of the present invention the cell clones used for the method of the present invention are mammalian cell clones, such as human or rodent cell clones. Particularly preferred are CHO cell clones, such as CHO-K1 cell clones or CHO-K1PD cell clones, which have been particularly analysed in the present case.

As mentioned previously, in preferred embodiments of the present invention the determining of the expression level in step a) involves quantitative RT-PCR. A person skilled in the art will understand, that the present invention contemplates in particular the specific detection and determination of the expression levels of the specific gene or genes selected from the group consisting of Hist1h2bc, Egr1, BX842664.2/Hist1h3c, Dhfr, Fgfr2, AC115880.11, Mmp10, CU459186.17, E130203B14Rik, Cspg4, C1qtnf1, Foxp2, Vsnl1 (optional) and Ptpre. Thus, step a) of the method of the present invention does preferably not involve complete transcriptome profiling, at least not for all clones tested.

The sequence of the genes selected from the group consisting of Hist1h2bc, Egr1, BX842664.2/Hist1h3c, Dhfr, Fgfr2, AC115880.11, Mmp10, CU459186.17, E130203B14Rik, Cspg4, C1qtnf1, Foxp2, Vsnl1 (optional) and Ptpre are known in the art and are publically available from respective databases. A person skilled in the art will be readily capable to design forward primers, reverse primers and probes in general for these genes and for the respective species of interest. For the Chinese hamster exemplary forward primers, reverse primers and probes are given for all 14 genes in table 1 further down below.

Once the relative expression level for the gene or genes has been obtained it should preferably be $\log_2$ transformed, i.e., in preferred embodiments of the invention the expression level is compared and the clone is selected on basis of relative expression values ($\log_2$ FC). The expression values should be normalized based on housekeeping or reference genes (e.g. GAPDH or ACTB, for which the expression is considered to be constant under all conditions) to render the obtained values also comparable between different experiments. For the statistical analysis the relative quantification approach can be used. Preferably, the geometric means of the Cq values of all reference genes are used as the final reference gene values.

In the inventive method, step b) requires selecting out of said at least two cell clones a cell clone for further expansion, whose expression level of said gene is with respect to the expression level of said same gene in at least one other clone tested in step a):
  i) upregulated, if the gene is a gene selected from the group of genes consisting of:
    Hist1h2bc, BX842664.2/Hist1h3c, Dhfr, AC115880.11, Fgfr2, Mmp10, Vsnl1 (optional) and, CU459186.17, or
  ii) downregulated, if the gene is a gene selected from the group of genes consisting of: Egr1, E130203B14Rik, Cspg4, C1qtnf1, Foxp2, and Ptpre.

As mentioned previously, there may be more than two cell clones, e.g. the selection can be made in some embodiments from at least 3, 4, 5, 6, 7, 8, 9, 10, 15, 20, 50, 75 or at least 100 or more candidate clones. The selection of the respective clone in step b) is straightforward based on the respective expression level if only for one gene the expression level is determined. The "at least one other clone tested in step a)" may be the clone with the worst expression level among the clones tested for said gene. Consequently, the method of the present invention allows in principle to choose the second worst candidate. While choosing the second worst candidate clone may not seem to be the most logical choice, said choice is still better than choosing the clone with the worst expression levels. Moreover, the second worst candidate clone may still exhibit excellent expression level values. In other words, the present invention allows eliminating at least the worst choice. However, in most circumstances where more than two clones are analysed the person skilled in the art will usually not select the second worst candidate, but one of the best candidates if not the best candidate, i.e. the clone exhibiting the best expression level for the respective gene. In the latter scenario the selected clone does not only exhibit a better expression level vis-à-vis "one other clone tested in step a)", but vis-à-vis all other tested clones. In preferred embodiments, the selected clone exhibits a better expression level vis-à-vis 50% of all other tested clones (above mean), more preferably 75% of all other tested clones, more preferably vis-à-vis 80% of all other tested clones, more preferably vis-à-vis 85% of all other tested clones, more preferably vis-à-vis 90% of all other tested clones, more preferably vis-à-vis 95% of all other tested clones, most preferably a better expression level than all other tested clones. Preferably, a clone is selected, whose expression level differs from the (mean) expression level of the same gene in the at least one other clone by at least a two-fold change ($\log_2$).

In a particularly preferred embodiment of the method of the invention a clone is selected in step b), whose expression level for Egr1, Hist1h2bc or Dhfr is superior to the expression level of said gene in at least one other clone tested in step a). In a further particularly preferred embodiment of the method of the invention a clone is selected in step b), whose expression levels for three genes selected from the group consisting of Fgfr2, BX842664.2/Hist1h3c, E130203b14Rik, Cspg4, Mmp10 or Ptpre taken together are superior to the expression level of said genes in at least one other clone tested in step a). Said group of genes has proven to be particularly useful, if MTX selection is applied.

As will be easily understood, the term "best expression level" (or "superior expression level") is a necessary relative term and its meaning will depend on the gene under scrutiny. For genes selected from the group consisting of Hist1h2bc, BX842664.2/Hist1h3c, Dhfr, AC115880.11, Fgfr2, Mmp10, Vsnl1 (optional) and CU459186.17 (upregulation group), a clone is selected exhibiting an upregulated (i.e. higher) expression level in comparison to the "at least one other clone tested in step a)". For genes selected from the group consisting of Egr1, E130203B14Rik, Cspg4, C1qtnf1, Foxp2, and Ptpre (downregulation group), a clone is selected exhibiting an expression level which is downregulated (i.e. lower). For the upregulation group the value of the clone with the lowest expression value can be set as reference value and the results for the other clones may then be expressed as fold change (FC) vis-à-vis said expression value. For the downregulation group the value of the clone with the highest expression value can be set as reference value and the results for the other clones may then be expressed as fold change (FC) vis-à-vis said expression value.

As mentioned above, while determining the expression level of one gene selected from the group consisting of Hist1h2bc, Egr1, BX842664.2/Hist1h3c, Dhfr, Fgfr2, AC115880.11, Mmp10, CU459186.17, E130203B14Rik, Cspg4, C1qtnf1, Foxp2, Vsnl1 (optional) and Ptpre is encompassed by the present invention, the present invention also contemplates determining the expression level of more than one gene. While in such scenario (more than one expression level determined) the subsequent selection decision can in principle be still be based on only one of the determined expression levels (i.e. not all expression levels determined need to be taken into account), said selection decision will usually be made by taking into account the results for more than one gene. As long as the genes are from the same group of genes (upregulation group: Hist1h2bc, BX842664.2/Hist1h3c, Dhfr, AC115880.11, Fgfr2, Mmp10, Vsnl1 (optional) and CU459186.17; downregulation group: Egr1, E130203B14Rik, Cspg4, C1qtnf1, Foxp2, and Ptpre) the expression level results can be simply taken together. If the expression level of genes from both groups are determined and are taken into consideration for the selection, then one must invert the algebraic sign for the values of one group, e.g. for the downregulation group (a −1.5 fold change in expression value (downregulation) is considered to be a (+) 1.5 FC), to allow combination of the expression values of the different groups. Eventually, a clone may be selected in such embodiments for further expansion, whose expression level taken together for said genes is superior to the level of said genes taken together in at least one other clone tested in step a).

In a particularly preferred embodiment of the method of the invention a clone is selected in step b), whose expression level is for two, or more preferably even for three genes selected from the group consisting of Egr1, Hist1h2bc and Dhfr superior (i.e. downregulated for Egr1, upregulated for Hist1h2bc and Dhfr to the expression level of said genes in at least one other clone tested in step a).

In other embodiments, a clone is selected in step b), whose expression level is for two, or more preferably even for three genes selected from the group consisting of Fgfr2, BX842664.2/Hist1h3c, E130203B14Rik, Cspg4, Mmp10 or Ptpre (or selected from the group consisting of Fgfr2, BX842664.2/Hist1h3c, E130203b14Rik, Cspg4, or Ptpre) taken together superior (i.e. downregulated for E130203b14Rik, Cspg4, or Ptpre, upregulated for Fgfr2, or BX842664.2/Hist1h3c) to the expression levels of said genes in at least one other clone tested in step a).

As previously for one gene, if more than one gene is used as basis for the selection decision, the selected clone exhibits preferably a better expression level vis-à-vis 50% of all other tested clones (above mean), more preferably better expression level vis-à-vis 75% of all other tested clones, more preferably vis-à-vis 80% of all other tested clones, more preferably vis-à-vis 85% of all other tested clones, more preferably vis-à-vis 90% of all other tested clones, more preferably vis-à-vis 95% of all other tested clones, most preferably a better expression level than all other tested clones. Thus, in an embodiment of the invention, a clone may be selected in step b) for further expansion, whose expression level for said genes is superior to the mean expression level taken together for said genes, respectively, as determined for two or more other clones tested in step a). Preferably, a clone is selected, whose expression level differs from the (mean) expression levels of the same genes in the at least one other clone by at least a two-fold change ($\log_2$).

As previously discussed, the selection in step b) of the method of the invention is based on a comparison of the expression level (or levels) of the selected clone with at least one other clone tested in step a). The selected clone must exhibit a "superior" expression level for the respective genes (up- or downregulated, depending on the gene(s) analyzed). However, the present invention also contemplates a selection of a clone on basis of an indirect comparison. In such scenario, a (first) clone may be selected indirectly on basis of a comparable or superior expression level for said gene (or expression levels taken together for said genes, respectively), as compared to at least one other clone tested in step a) (the second clone), provided said at least one other clone (the second clone) has been previously verified to have a superior expression level for said gene (or expression levels taken together for said genes, respectively), as compared to at least one further clone (third clone) tested in step a). In other words, if previously an advantageous clone (the second clone) has already been identified (advantageous vis-à-vis the third clone), then the new (first) clone can be selected already on basis of a comparable (or superior) expression level vis-à-vis the second clone, because the new (first) clone will inevitably fulfil the criterion of having an advantageously up- or downregulated expression level for the respective gene or genes vis-à-vis the third clone.

The method according to the present invention is certainly not limited to selecting only one clone. Rather, more than one cell clone may be selected on basis of the prerequisites of step b) for further expansion.

In preferred embodiments of the invention the expression level of at least three genes selected from the group consisting of Hist1h2bc, Egr1, BX842664.2/Hist1h3c, Dhfr, Fgfr2, AC115880.11, Mmp10, CU459186.17, E130203B14Rik, Cspg4, C1qtnf1, Foxp2, Vsnl1 (optional) and Ptpre, is determined and the selection in step b) is made by using a three dimensional representation of the results. The three genes can be for instance Egr1, Hist1h2bc and Dhfr. In some embodiments, in particular of MTX selection is used, the three genes are preferably selected from the group consisting of Fgfr2, BX842664.2/Hist1h3c, E130203b14Rik, Cspg4, Mmp10 and Ptpre. More preferably, the three genes are selected from the group consisting of Fgfr2, BX842664.2/Hist1h3c, E130203b14Rik, Cspg4, and Ptpre.

The selection in step b) can also be made by using principal component analysis of the expression levels of the genes analysed in step a) and using the first three principal components for a three dimensional representation of the results.

Furthermore, the method of the present invention requires selecting out of said at least two cell clones a cell clone for "further expansion". As used herein, "for further expansion" is intended to specify, that cell culture of the respective clone is not discontinued. Rather culture of said clone is preferably continued until reliable productivity measurements can be made. Moreover, the clone is ideally even expanded (increase in cell number and/or culture volume) for large scale protein production.

The method of the present invention may therefore comprise the additional step of:

c) expanding said selected cell clone.

In embodiments where MTX selection is employed, the selected cell clone may for example be expanded in MTX selection medium.

The method of the present invention is not practiced on the human or animal body, i.e. it is an ex vivo or in-vitro method, respectively, as will be readily understood by the person skilled in the art.

In a second aspect, the present invention relates to a host cell for recombinant protein expression, the host cell exhibiting artificially modified gene expression of at least one gene selected from the group consisting of:

Hist1h2bc, Egr1, BX842664.2/Hist1h3c, Dhfr, Fgfr2, AC115880.11, Mmp10, CU459186.17, E130203B14Rik, Cspg4, C1qtnf1, Foxp2, Vsnl1 (optional) and Ptpre, wherein the gene expression is:

i) artificially upregulated, if the gene is a gene selected from the group of genes consisting of:

Hist1h2bc, BX842664.2/Hist1h3c, Dhfr, AC115880.11, Fgfr2, Mmp10, and, CU459186.17, and/or ii) artificially downregulated (e.g. silenced or knocked-out), if the gene is a gene selected from the group of genes consisting of: Egr1, E130203B14Rik, Cspg4, C1qtnf1, Foxp2, and Ptpre.

For instance, a host cell according to the present invention may exhibit artificially modified gene expression of at least one gene selected from the group of genes consisting of: Hist1h2bc, BX842664.2/Hist1h3c, Dhfr, AC115880.11, Fgfr2, Mmp10, Vsnl1 (optional) and, CU459186.17, and the gene expression is artificially modified by overexpressing the respective gene or genes. Overexpression may be achieved by conventional means in the art, e.g. by (stable or transient) transfection with additional copies of said gene or be manipulation of respective regulatory means (e.g. change of promoter, removal of regulatory sequences etc.). A host cell of the present invention may also exhibit artificially modified gene expression of at least one gene selected from the group consisting of Egr1, E130203B14Rik, Cspg4, C1qtnf1, Foxp2, and Ptpre, wherein the gene expression is artificially modified (i.e. downregulated) by (transient or stable) knockdown, knockout and/or silencing of the respective gene or genes. In general, if gene expression for more than one gene is modified, then this may be achieved by the same means (e.g. all are knocked down, or by different means (e.g. one is knocked out, one is knocked down).

Preferably, the host cell is a mammalian host cell, such as human host cell or a rodent host cell. Particularly preferred are CHO cells, such as CHO-K1 cells or CHO-K1PD cells. The host cell of the present invention is preferably an isolated host cell and thus not part of an intact higher organism.

The host cell of the invention is for recombinant protein production but need not yet be transfected with the recombinant gene encoding the recombinant protein. However, in some embodiments, the host cell comprises a recombinant gene encoding a recombinant protein. The recombinant gene may encode any type of recombinant protein. The recombinant protein may be for example an antibody, antibody light or heavy chain, a toxin, a cytokine, a growth factor, a growth factor receptor, an enzyme, or a hormone. Preferably, the recombinant protein is an antibody.

It is understood that embodiments discussed above for the inventive method also apply in the context of the inventive host cell, for instance with respect to the number of genes modified (e.g. at least 2, at least 3, at least 4, at least 5, at least 6, at least 7, at least 8, at least 9, at least 10, at least 11, at least 12, at least 13 or all 14 genes), preferred genes and groups of genes (e.g. Egr1, Hist1h2bc and Dhfr; or, e.g., Fgfr2, BX842664.2/Hist1h3c, E130203b14Rik, Cspg4, Mmp10 and Ptpre, or Fgfr2, BX842664.2/Hist1h3c, E130203b14Rik, Cspg4, and Ptpre) etc.

The term "comprising", as used herein, shall not be construed as being limited to the meaning "consisting of" (i.e. excluding the presence of additional other matter). Rather, "comprising" implies that optionally additional matter, features or steps may be present. The term "comprising" encompasses as particularly envisioned embodiments falling within its scope "consisting of" (i.e. excluding the presence of additional other matter) and "comprising but not consisting of" (i.e. requiring the presence of additional other matter, features or steps), with the former being more preferred.

The use of the word "a" or "an", when used herein, may mean "one," but it is also consistent with the meaning of "one or more," "at least one," and "one or more than one." In particular, "determining . . . the expression level of a gene" selected from the inventive group does not preclude determining the expression level of another gene from said group or of other genes not within this group. Likewise, "selecting a cell clone" may refer to selecting only one cell clone, but does not exclude selecting more than one cell clone.

"A suitable candidate cell clone", as used herein, will be preferably a cell clone exhibiting long-term stability of recombinant protein expression, i.e. with a drop in productivity over a period of 10 weeks of no more than 30% and/or a a drop of copy number of the recombinant gene by not more than 50% in the same time period.

EXAMPLES

In the following, specific examples illustrating various embodiments and aspects of the invention are presented. However, the present invention shall not to be limited in scope by the specific embodiments described herein. Indeed, various modifications of the invention in addition to those described herein will become readily apparent to those skilled in the art from the foregoing description, accompanying figures and the examples below. All such modifications fall within the scope of the appended claims.

Example 1: General Outline of the Experiment

The inventor of the present invention has established a transcriptome profile of CHO cell clones with stable and unstable recombinant protein (an antibody) production in an over 10-weeks long study. The main purpose of the study was to identify marker genes related to stable expression of the recombinant gene. The same clones were cultivated for 10-weeks in parallel with and without MTX as a selection pressure in the media. The general set up of the experiments is depicted in FIG. 1.

Total RNA (tRNA) was isolated weekly from each clone for transcriptome profiling by using DNA microarray and RT-qPCR. The transcript profile of clones with stable and unstable recombinant protein production in 10-week long cultivation was performed using DNA microarray with 61.223 probes. The number of transcripts was reduced to 14 differently expressed genes which were selected for further verification using RT-qPCR method. The expression of the top 14 differently expressed genes based on DNA microarray results was verified by RT-qPCR on all clones. The expression of each gene was verified using RT-qPCR in triplicates.

Example 2: Detailed Outline of the Experiment

An expression vector was constructed comprising an recombinant protein (antibody), antibiotic resistance and recombinant Dhfr (rDhfr) gene. The linearised expression vector was transfected into the host cell line using the nucleofection method (Nucleofector, Lonza) according to the manufacturer's protocol. After transfection, antibiotic selection was performed, followed by amplification of the recombinant gene by MTX (methotrexate hydrate). Cloning was performed using ClonePix FL technology (Molecular Devices).

Samples from antibody-secreting clones derived from a single cell line (CHO-K1PD) were collected for gene expression profiling. All clones were split in two series. One series was grown with MTX and the second series in the absence of MTX in the media. The culture was collected weekly. Samples originating on week 1 and 2 were pooled together for data analysis and marked as "beginning". Also the samples originating on week 9&10 were pooled together and marked as "end".

Serum free media, supplemented with 8 mM of L-glutamine, was used in both series. All clones were cultivated for additional 10 weeks. To confirm that clones under investigation varied only in terms of presence or absence of MTX, each culture was cultivated under the same environmental conditions (37° C., 10% $CO_2$, 30 ml working volume in shake flasks).

On every passage, 1 ml of culture was taken to assess viable cell density and cell viability using the automated cell counter (Vicell, Beckmann Coulter). Every week a batch process has started for all clones. Productivity was determined by Octet automated system according to the manufacturer's protocol (Forte Bio). Each clone was passaged twice per week, using seeding density of $2 \times 10^5$ cells/ml.

Example 3: Cell Culture

Host Cells

Parental CHO-K1PD cell lines were used in the experiment. The CHO-K1PD cell line is a subpopulation of the CHO-K1 cell line which originates from ATCC (Cat. No. CCL-61.3). The original cell line was adapted to serum free suspension culture and underwent 3 successive rounds of selection at increasingly dilute seeding densities to improve the frequency of serum-free subcloning in DM122 medium (Irvine Scientific). Recombinant producing cell lines were prepared by transfection of the CHO-K1PD with the expression vector.

Nucleofection

The Amaxa nucleofection system was used for cell transfection (Nucleofector kit V), according to the manufacturer's protocol and programme U23 for transfection (Amaxa). Not more than 5 pools are transfected at once, to enable sufficient time for all necessary cell manipulations.

Growth Medium

CHO-K1PD cells were cultivated in DM122 growth medium (Irvine Scientific) supplemented with 8 mM L-glutamine (Sigma). Cell selection steps were performed in the same medium additionally supplemented with geneticin (G418, Gibco). Metothrexate hydrate (Sigma) was added in the medium where applicable.

Culture and Handling of Cells

Cells were passage on 3-4-3 day period for 10 weeks. On every passage, 1 ml of culture was taken to assess viable cell density and cell viability using the automated cell counter (Vicell, Beckmann Coulter). Every week a batch process was started for all clones. Productivity was determined by automated system according to the manufacturer's protocol (Forte Bio, Octet). Each clone derived sample was passaged twice per week, using a seeding density of $2 \times 10^5$ cells/ml.

Samples of tRNA/gDNA were taken weekly on day 3 after passage in exponential growth phase.

Incubation conditions: 37° C., for 125 ml shake flasks and 10% $CO_2$.

Example 4: DNA Microarray

RNA Isolation

The samples for RNA isolation were taken weekly on day 3 (early log phase), after the passage. Total RNA was isolated by automated QiaCube (Qiagen) system using Rneasy Mini Kit (Qiagen), following the manufacturer's protocol. RNA was examined by ND-1000 Spectrophotometer (NanoDrop Technologies) and RNA integrity was checked by Agilent RNA Nano chip on Bioanalyzer 2100 (Agilent).

Hybridization

Before being hybridized to proprietary CHO specific DNA microarray (manufactured by Affymetrix) all mRNA was diluted appropriately to the same concentration. Biotinylated cRNA was prepared according to the protocol described in the Affymetrix technical manual.

The expression DNA microarray consist of 61.223 probe sets, targeting approximately 26.227 Chinese hamster unique gene IDs and 14,657 unique Ensembl mouse genes. cRNA was synthesized from cDNA using the 3'-IVT Express kit (Affymetrix). Subsequent hybridization onto the custom microarray was performed in the GeneChip Hybridization Oven 640 (Affymetrix) and the processing was done using the GeneChip Fluidics Station 450 (Affymetrix).

Statistical Analysis of DNA Microarray Data

The raw image files were processed using the GeneSpring GX software (Agilent Technologies) and normalised using the robust multichip average algorithm. Further the RMA baseline to median normalisation was performed (using GeneSpring software). All further statistical analysis was performed in the bioconductor using package limma. In order to reduce the extent of false positive results, we have filtered out the non-expressed genes (expression value below background in at least 80% of all samples). Empirical Bayes modelling, taking into account the stability of recombinant protein production and the presence of MTX, was used to detect differentially expressed genes between the different clones. By comparing the transcriptome profile of stable and unstable group of clones, 295 differently expressed genes (corrected P value<0.05) were identified The samples for gene expression pre-analysis were divided into two main groups—clones with stable recombinant protein production and clones with unstable recombinant protein production. The clones were considered to be unstable if productivity dropped for more than 30% over the period of 10 weeks and if recombinant gene copy number dropped by more than 50% in the same time period.

Example 5: Quantitative Real-Time PCR (RT-qPCR)

5.1 Gene Expression

RNA Isolation, DNAseI Reaction and RT-Reaction

The same total RNA was used for quantitative qPCR analysis as it was used for DNA microarray. An additional step of genomic DNA removal using Dnase I (Ambion) was performed prior to cDNA synthesis. DNaseI was added to 5 µg of total RNA (tRNA) and incubated (25 min 37° C., 10 min 75° C.). After DNase treatment RNA was transcribed into cDNA using SuperScript VILO kit (Invitrogen) according to the manufacturer's protocol. After DNase treatment RNA was transcribed into cDNA using SuperScript VILO kit (Invitrogen) according to the manufacturer's protocol.

Sample Preparation for Gene Expression (RT-qPCR)

The top 14 differentially expressed genes from the microarray data were groundwork for further verification using quantitative real-time PCR (RT-qPCR). Primer pairs and probes were designed in the region of microarray oligo design to ensure the compatibility of results between both platforms. Details of the primer/probe design is described in Table 1 below.

Table 1a to d: Details of the primer/probe design for all 14 genes used for RT-qPCR.

TABLE 1a

| Gene symbol | Gene Description | Gene ID |
|---|---|---|
| Fgfr2 | fibroblast growth factor receptor 2 | ENSMUSG00000030849 |
| BX842664.2/ Hist1h3c | histone cluster 1, H3c | N.A. |
| AC115880.11 | not annotated | N.A. |
| E130203B14Rik | not annotated | ENSMUSG00000050666 |
| hDHFR | hamster dihydrofolate reductase | N.A. |
| Hist1h2bc | histone cluster 1, H2bc Gene | ENSMUSG00000018102 |
| Cspg4 | chondroitin sulfate proteoglycan 4 Gene | ENSMUSG00000032911 |
| C1qtnf1 | C1q and tumor necrosis factor related protein 1 | ENSMUSG00000017446 |
| Foxp2 | forkhead box P2 Gene | ENSMUSG00000029563 |
| Mmp10 | matrix metallopeptidase 10 | ENSMUSG00000047562 |
| Vsnl1 | visinin-like 1 | ENSMUSG00000054459 |
| CU459186.1 | Mouse DNA sequence, clone RP23-293P3, chromosome 2 | N.A. |
| Egr1 | early growth response 1 Gene | ENSMUSG00000028688 |
| Ptpre | protein tyrosine phosphatase, receptor type E | ENSMUSG00000041836 |

TABLE 1b

Forward primer sequences (5'-3') used for the RT-qPCR.

| Gene | Sequence | SEQ ID NO: |
|---|---|---|
| Fgfr2 | GCCTGAGTTACACATCCATCACA | 1 |
| BX842664.2/ Hist1h3c | GGCCCAGACATGGACACT | 2 |
| AC115880.11 | CGAGCTTTTCACCAGTAGAGATAGTTA | 3 |
| E130203B14Rik | CCAGTGGGTACATCACATGAGAGA | 4 |
| hDHFR | ATATGGGGATTGGCAAGAACG | 5 |
| Hist1h2bc | ACGAGGAGTAGACCTGATGATGT | 6 |
| Cspg4 | GCCATGTGGCCTAGCTTCAT | 7 |
| C1qtnf1 | CATTCCACAGACACTGGATGGA | 8 |
| Foxp2 | GGGCTTACGGCTTATACTCTATGTG | 9 |
| Mmp10 | CAGGAATCGAGCCACAAATTGATG | 10 |
| Vsnl1 | ACCCTTAAGCATATGTCTTTGGAATTTGA | 11 |
| CU459186.1 | GGGAGGCCGGTTTTGG | 12 |

TABLE 1b-continued

Forward primer sequences (5'-3') used for the RT-qPCR.

| Gene | Sequence | SEQ ID NO: |
|---|---|---|
| Egr1 | GCTCACCTCTGGCCTTAAAGG | 13 |
| Ptpre | CCCTCCAGTCTCTTGGCTAATG | 14 |

TABLE 1c

Reverse primer sequences (5'-3') used for the RT-qPCR.

| Gene | Sequence | SEQ ID NO: |
|---|---|---|
| Fgfr2 | GATGATGAAGGTCCTGAAGCTGTTA | 15 |
| BX842664.2/ Hist1h3c | CCATGAGGCACTGGGACTTT | 16 |
| AC115880.11 | TTGACACATACAGCTCCAATTCCA | 17 |
| E130203B14Rik | CCCGAGTGGGAGCTGACT | 18 |
| hDHFR | CATTCTTTGGAAGTACTTGAACTCGTT | 19 |
| Hist1h2bc | GTATCACCTATTTCCATTGTCTCAATTGC | 20 |
| Cspg4 | AAACAGGTGAGAATAGAGGACTTTGG | 21 |
| C1qtnf1 | GCCAAAGAAGCCAGGACTGA | 22 |
| Foxp2 | CCCAGTTAGTGGTAATTCTATCAAGTACTTT | 23 |
| Mmp10 | TCAAACTGTGATGATCCATGGAAGAA | 24 |
| Vsnl1 | TTCCGAAATGAACAAATCGTCTGTT | 25 |
| CU459186.1 | TTGTGCAACACCCAGAGACTAC | 26 |
| Egr1 | CATTCTGGAGAACCAAAGCT | 27 |
| Ptpre | GCAAACTGAGTCTCTGTGTCTTAGG | 28 |

TABLE 1d

Probe sequences (5'-3') used for the RT-qPCR.

| Gene | Sequence | SEQ ID NO: |
|---|---|---|
| Fgfr2 | TTGGCCTCACATCTCC | 29 |
| BX842664.2/ Hist1h3c | AAGCGCCCCATCAGC | 30 |
| AC115880.11 | ACGGGCTTCAGTCTTC | 31 |
| E130203B14Rik | AAACTGTGCCAAACTC | 32 |
| hDHFR | AGACCTACCCTGGCCT | 33 |
| Hist1h2bc | CAGTGCTGGACGTTGTT | 34 |
| Cspg4 | CAAGCTCTTGAATTCC | 35 |
| C1qtnf1 | CTGACCCCATCATCCC | 36 |
| Foxp2 | ACGGTGCCATGAATCC | 37 |
| Mmp10 | AATGCCTGCAACACCG | 38 |

TABLE 1d-continued

Probe sequences (5'-3') used for the RT-qPCR.

| Gene | Sequence | SEQ ID NO: |
|---|---|---|
| Vsnl1 | TCATCCAGCCCCTCCC | 39 |
| CU459186.1 | TTGCTGCCCGGTATCC | 40 |
| Egr1 | CAGCTCAGCCCTCTTC | 41 |
| Ptpre | CCACAACCAAATTCAG | 42 |

TaqMan-MGB® probes were designed for all genes and manufactured at Life Technologies. All RT-qPCR reactions were performed on an ABI PRISM® 7900 Sequence Detection System (Life Technologies) in 384-well plate format using universal cycling conditions (2 min at 50° C., 10 min at 95° C., followed by 45 cycles of 15 s at 95° C. and 1 min at 60° C.) which allowed all reactions to be run on the same plate. Each sample DNA was tested with: 14 target genes and two endogenous controls (ACTB, GAPDH). Each reaction was performed in three replicate wells in two dilutions on the same 384-well plate. QIAgility automated liquid handling system (Qiagen) was used to prepare cDNA dilutions and to pipette large numbers of cDNA samples and master mixes onto the 384-well plates.

Statistical Analysis

The dilution factors were determined individually for each amplicon on a subset of samples, in order for the quantification cycle (Cq) values to be in the range 22-34. The software SDS 2.1 (Life Technologies) was used for fluorescence acquisition and Cq calculation. For this calculation, the baseline was set automatically and the fluorescence threshold set manually (0.1) to intersect with the linear part of the amplification curves of all amplicons in all runs. The relative quantification approach was used basically as described in Pfaffl (Pfaffl M W, 2001, Nucleic Acids Res, Vol. 29; No. 900). Each sample was analysed in two dilutions and three replicates per dilution step. Only samples where the ΔCq between two dilutions of target gene did not deviate by more than 0.5 from ΔCt of the reference gene were used for relative quantification. Additionally, the ΔCq values between the two dilutions of cDNA were calculated for each sample and used to calculate approximate amplification efficiencies (E=10[1/ΔCq]) for each sample individually. These sample-specific efficiencies were used in the relative quantification formula.

The geometric mean of Cq values of separate reference gene was used as the final reference (see Vandesompele J et al., 2002, Genome Biol, 3 (7)). A relative expression ratio was calculated separately for each dilution of each sample and averaged to yield the final relative expression ratio for the sample. The ratio was then $\log_2$ transformed.

The Welch two sample t-test was used to determine statistically significant differences between relative expression ratios of stable and unstable clones with a P=0.05 as the limit for statistical significance. Based on the data obtained by RT-qPCR the most differently expressed genes between the stable and unstable samples were shown using a three-dimensional representation (MATLAB2014). In this three-dimensional representation, the properties of the clones were described by the expression of three genes. The expression of each of these three genes was related to each of the three separate axes, hence providing a three-dimensional representation of the samples.

To systematically evaluate the separation of unstable and stable clones the k-nearest neighbour clustering algorithm was used on the data used for the three-dimensional representation (Seber G A, 1984). The algorithm uses unsupervised learning where the goal is to separate the data into a predefined number of classes while no information on class membership of each training sample is provided. The algorithm minimizes the sum of squared Euclidian distances between members and centroids of the classes. As a result the most likely class centroids and its members are estimated. The rate of correctly classified samples was taken as a measure for separation of the stable and unstable groups on the basis of gene expression data of the three genes. The k-means function of MATLAB2014 (The Mathworks Inc.) was used for the task.

5.2) Recombinant Gene Copy Number

DNA Isolation

The genomic DNA (gDNA) from all clones was isolated using DNA Blood Kit (Qiagen) with automated system for DNA isolation (QiaCube, Qiagen), according to the manufacturer's protocol. gDNA was quantified by ND-1000 Spectrophotometer (NanoDrop Technologies).

Copy Number

Copy number of recombinant gene was determined by RT-qPCR (ABI PRISM 7900, Applied Biosystems/Life Technologies) on all samples. QIAgility automated liquid handling system (Qiagen) was used to prepare DNA dilutions and to pipette large numbers of DNA samples and master mixes onto the 384-well plates. TaqMan-MGB® probes for all genes were designed and manufactured at Life TechnologiesPrimer-probe mix were designed and manufactured at Life Technologies. All reactions were performed in triplicates.

Data Analysis

Copy number of recombinant gene was calculated using absolute quantification method. Standard curve was constructed by using the DNA of the same expressed vector, as it was used for transfection of host cell line and gDNA of parental host cell line. The software SDS 2.1 (Life Technologies) was used for fluorescence acquisition and Cq calculation. Copy numbers of recombinant gene and Gluc (endogenous Glucagon gene) in the sample were extrapolated from the standard curves. The ratio between endogenous gene Gluc (single copy gene) and recombinant gene was calculated for determination of the recombinant gene copy number per cell.

Example 6: Results

Figure 3:
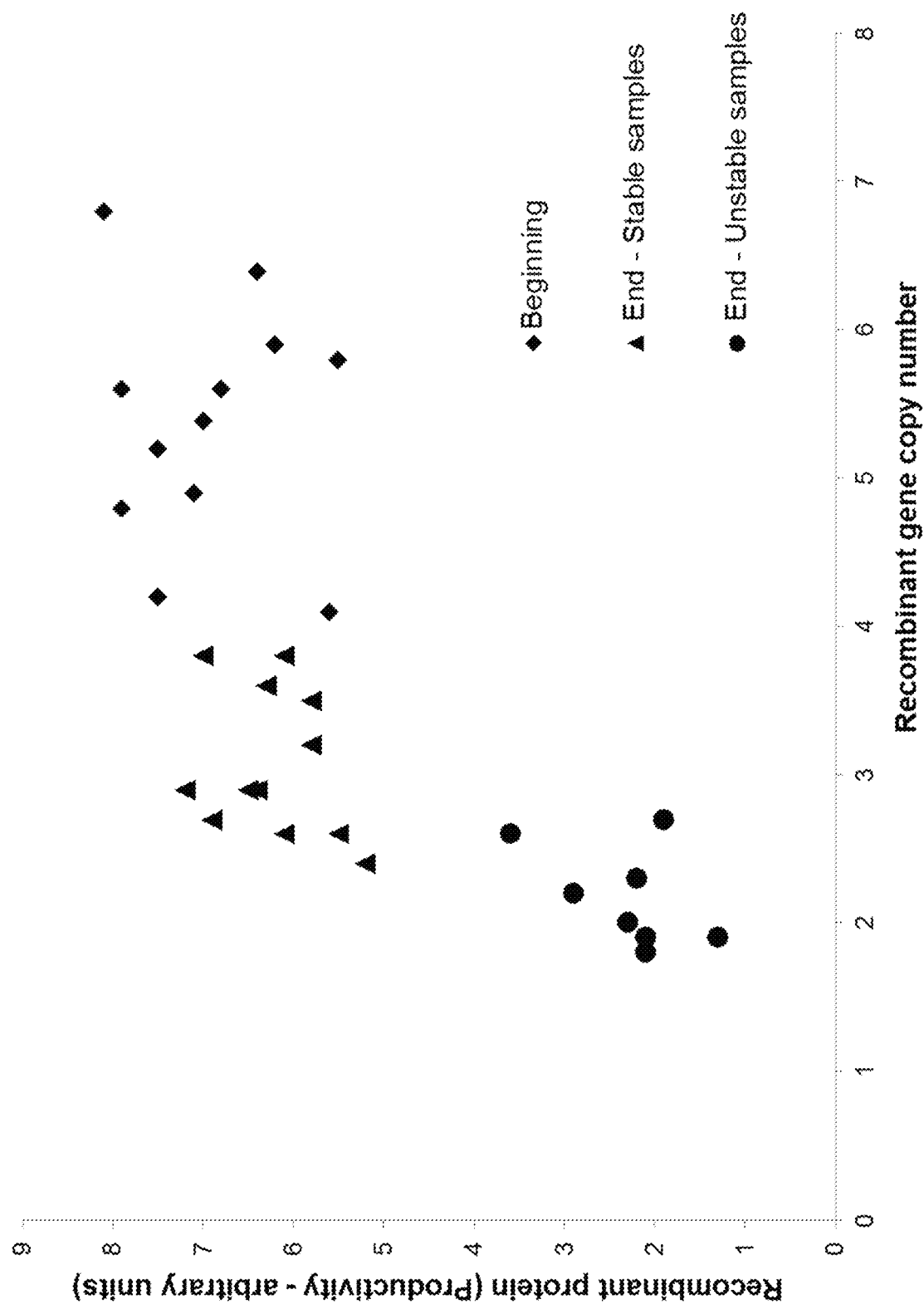

During 10 week long study productivity declined for 67% (7.0 to 2.3 arbitrary units) and recombinant gene copy number per cell declined for 61% (5.4 to 2.1 copy of recombinant gene per cell) in all clones without MTX in the media (FIG. 3). At the same time, productivity on average declined only for 9% (7 to 6.4 arbitrary units) and recombinant gene copy number per cell declined for 45% (5.4 to 3 copies of recombinant gene per cell) in clones with MTX in the media.

Based on the decline of productivity over 10 week long study 2 groups of clones were formed. Clones with stable recombinant protein production lost 9% of initial productivity over 10 weeks, compared to unstable clones where productivity dropped for 67% during the same time period (FIG. 3).

By comparing the transcriptome profile of stable and unstable group of clones, 295 differently expressed genes (adjusted P value<0.05) were identified. As all unstable productivity results were obtained when selection pressure was not present (no MTX in the medium), these results have been compared with the effect of cultivating cells without or with MTX. 199 genes were identified as differentially expressed between group of clones without and with MTX in the medium (adjusted P value<0.05) and 83 genes were common to both group of clones. Remaining 212 genes were specifically differentially expressed only between stable and unstable clones and were therefore the focus of our further research.

Expression profile of 14 top differentially expressed genes between stable and unstable clones (log $FC_{abs}$>0.8, adjusted P-value<0.05) was verified using RT-qPCR: Fgfr2, BX842664.2/Hist1h3c, AC115880.11, E130203b14Rik, hDhfr, Hist1h2bc, Cspg4, C1qtnq, Foxp2, Mmp10, Vsnl1, CU459186.17, Egr1, and Ptpre. Among them Fgfr2, BX842664.2/Hist1h3c, E130203b14Rik, Cspg4, Mmp10, Vsnl1, and Ptpre were identified as not affected by presence of MTX.

Figure 2:
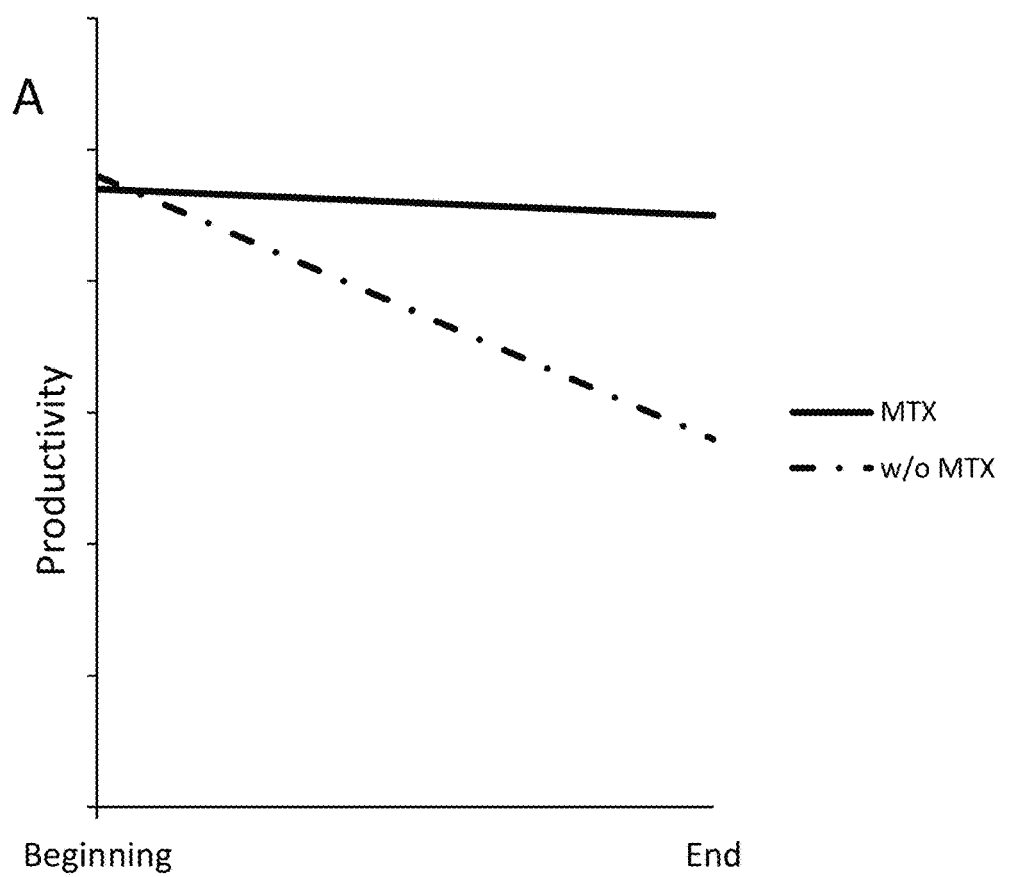
Figure 2:
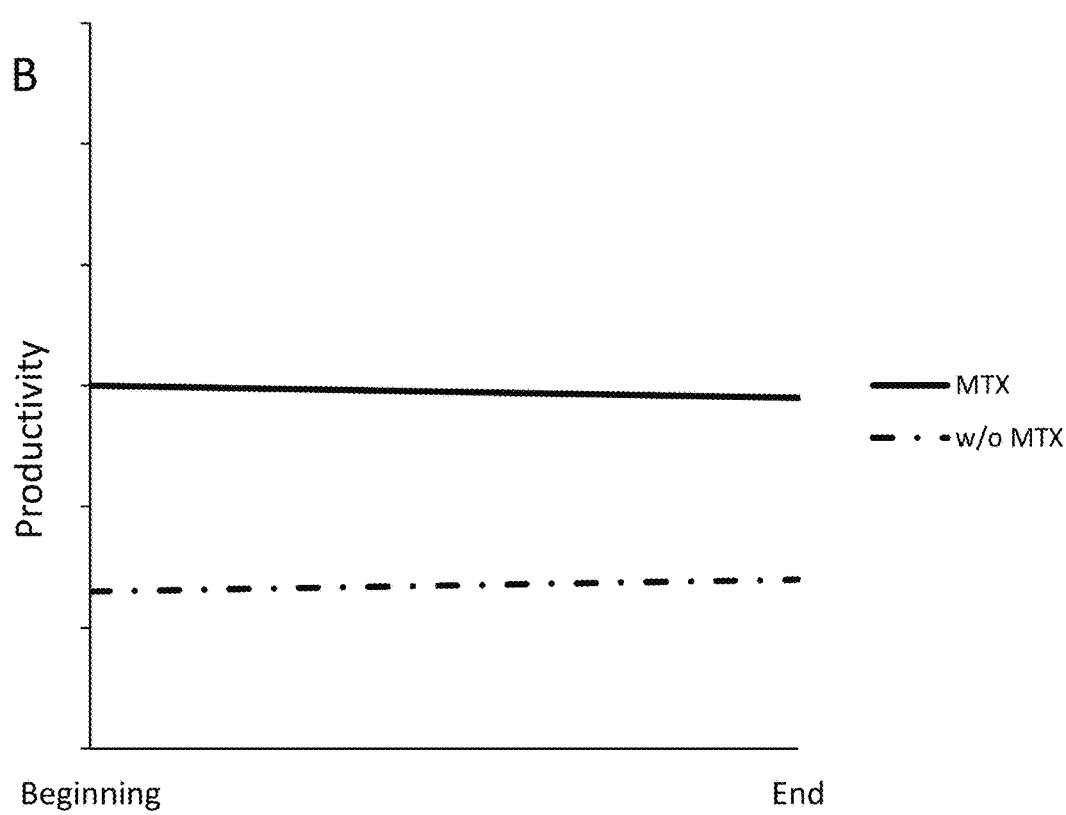
Figure 4:
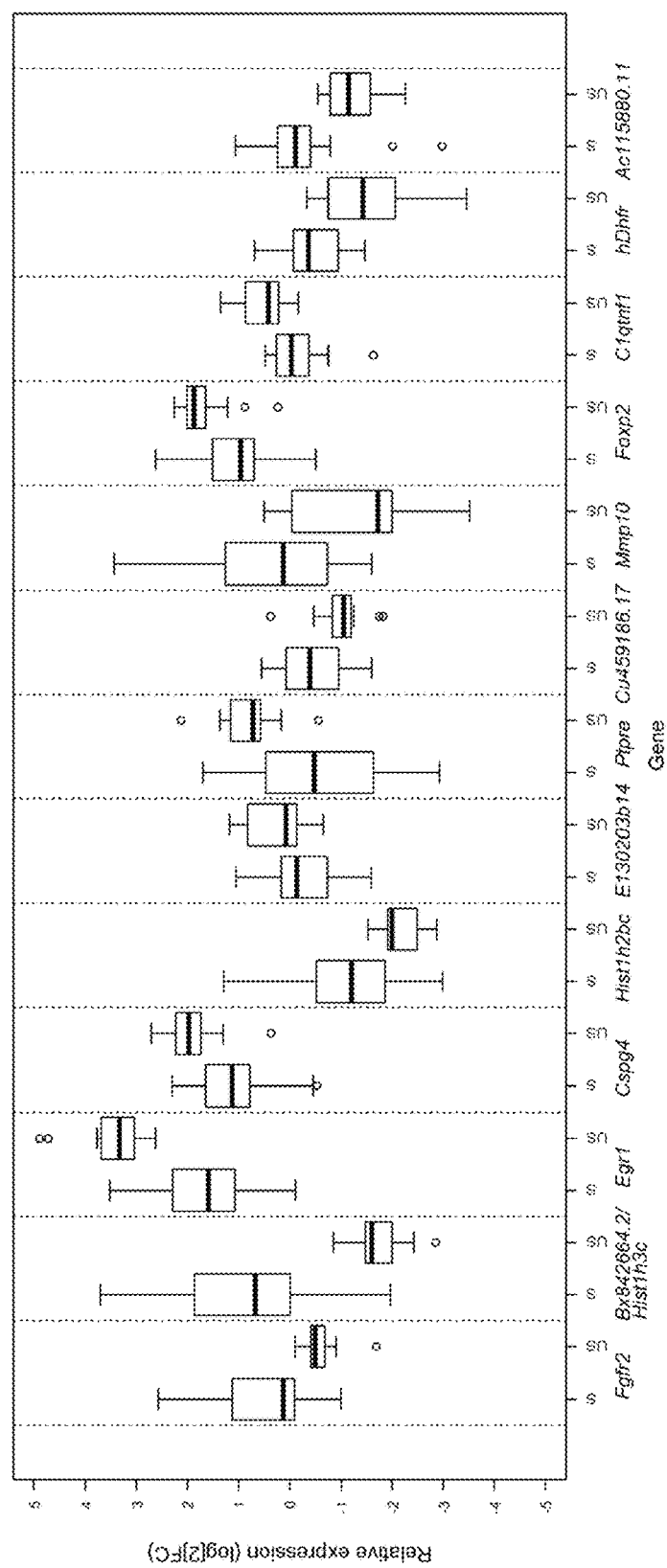

First comparison of gene expression pattern between stable and unstable producing clones, regardless of their sampling time point, revealed 13 out of 14 genes with differentially expression pattern (FIG. 2). 13 out of 14 genes have a P-value<0.05, except gene Vsnl1 has P-value>0.05. 8 out of 14 tested genes were up-regulated (Fgfr2, BX842664.2/Hist1h3c, AC115880.11, hDhfr, Hist1h2bc, Mmp10, Vsnl1, CU459186.17) and 6 gene (E130203B14Rik, Cspg4, C1qtnf1, Foxp2, Egr1, Ptpre) were down regulated in stable clones. The expression values for each gene are represented in Box whisker plot (BWP) for stable and unstable clones separately (FIG. 4). The biggest difference in median of differently expressed gene between stable and unstable clones was observed for BX842664.2/Hist1h3c ($\log_2$ FC=2), Egr1 ($\log_2$ FC=2), hDhfr ($\log_2$ FC=1), Hist1h2bc ($\log_2$ FC=0.7).

Figure 5:
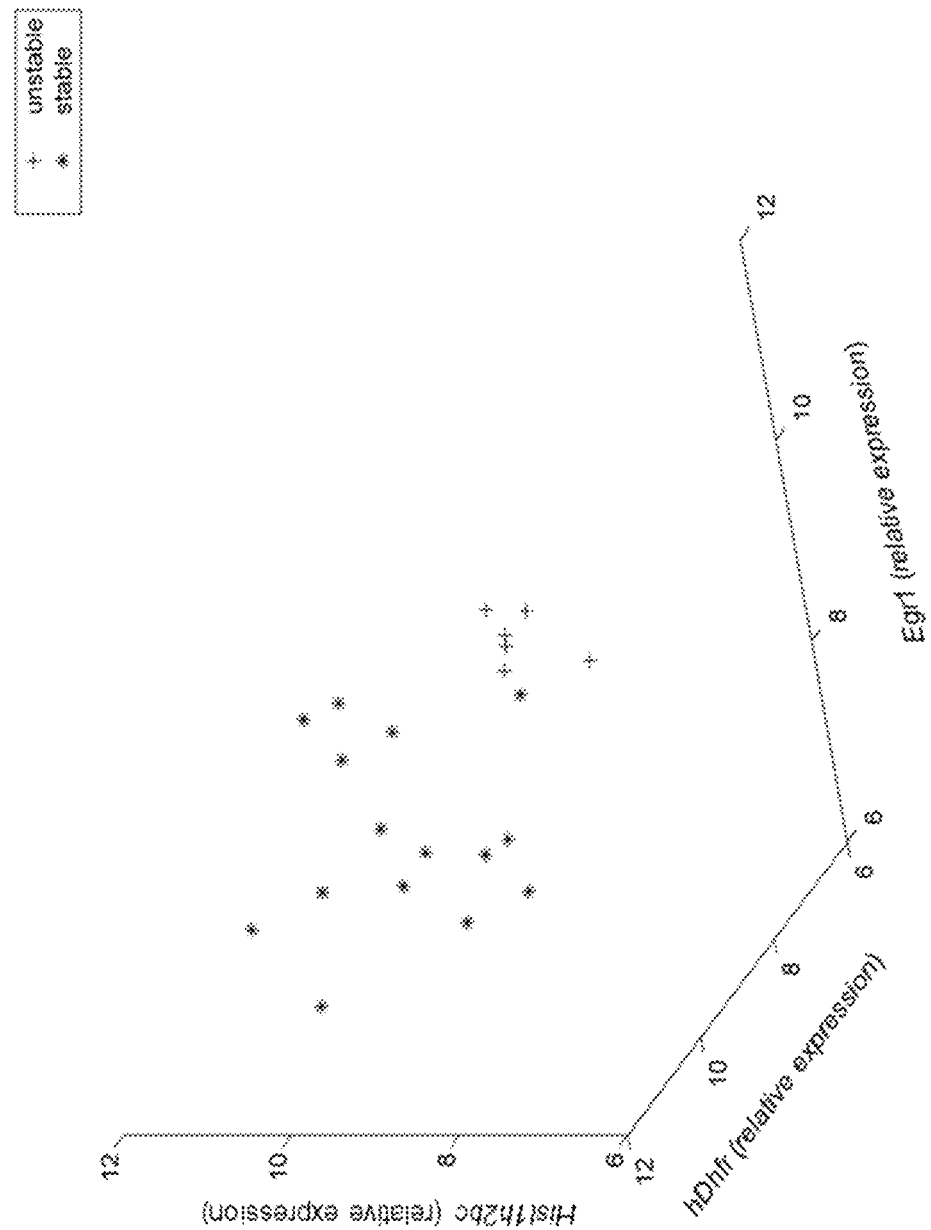
Figure 7:
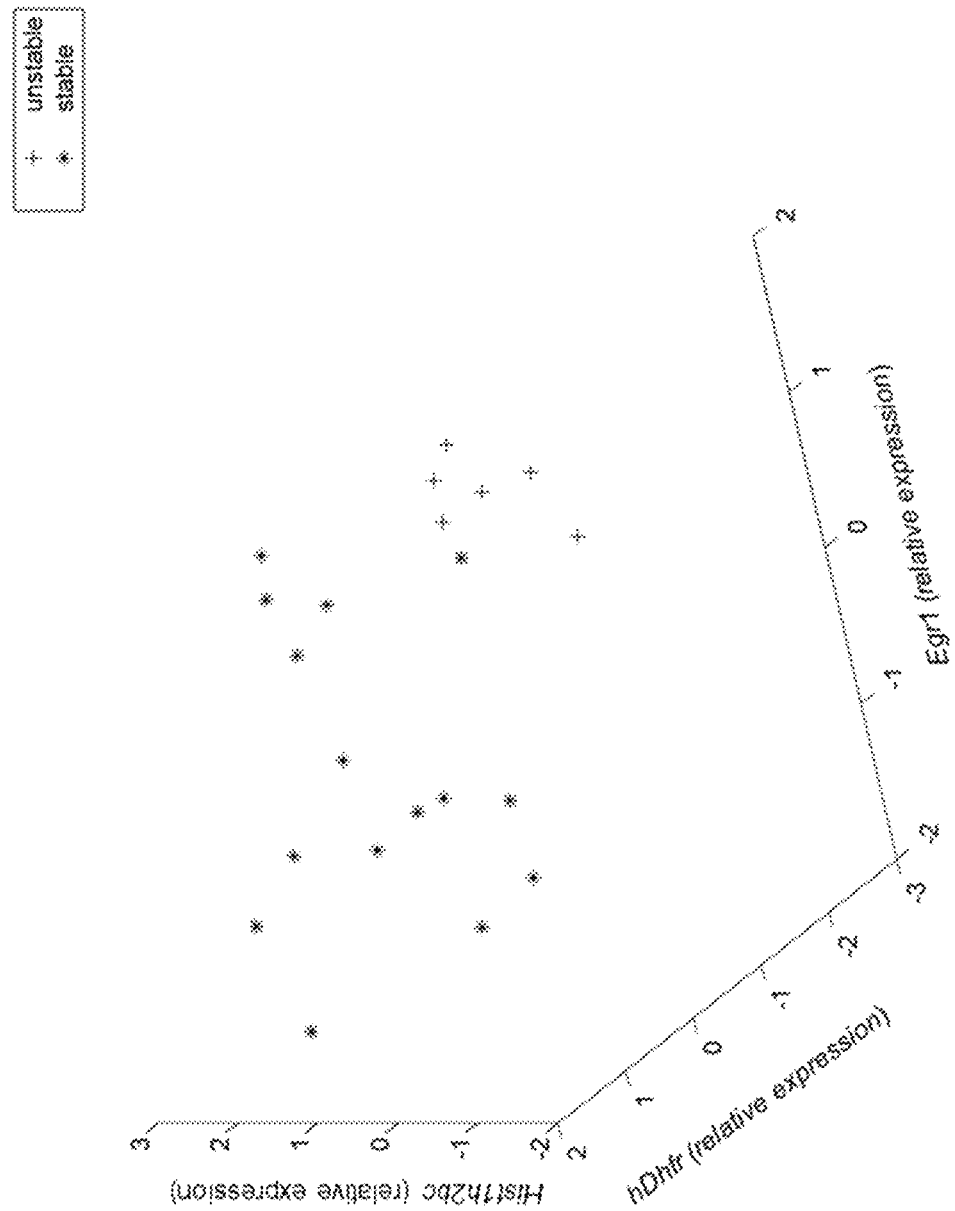
FIG. 7 is a three-dimensional representation corresponding to the data of FIG. 5, the data being plotted for three genes hDhfr (hamster Dhfr), Egr1, Hist1h2bc. The mean of relative expression values for each gene were calculated and then the mean was subtracted from the gene expression from each sample.

Based on the differently expressed genes among stable and unstable clones the inventor selected 3 genes (Egr1; $\log_2$ FC=2, hDhfr $\log_2$FC=1, Hist1h2bc; $\log_2$ FC=0.7) for three-dimension representation with the MATLAB2014 (The Mathworks Inc.). The 15 stable and 6 unstable samples that originated from the beginning of the genetic stability study are shown in FIG. 5. The properties of these clones can thus be described by the gene expression of each of these three genes. Each level of gene expression is presented in FIG. 5 according to its own separate axis, hence providing a three-dimension representation of these samples. In this three-dimension representation shown in FIGS. 5 and 7 there is clear separation of the two groups, as stable and unstable, with only one false negative. The classification with the k-nearest neighbour algorithm also confirmed the separation of the two groups. For early stage of growth (beginning) the algorithm correctly classified 85% of the samples (only three false negative results) and for the late stage (end) the classification success was 71%.

Figure 6:
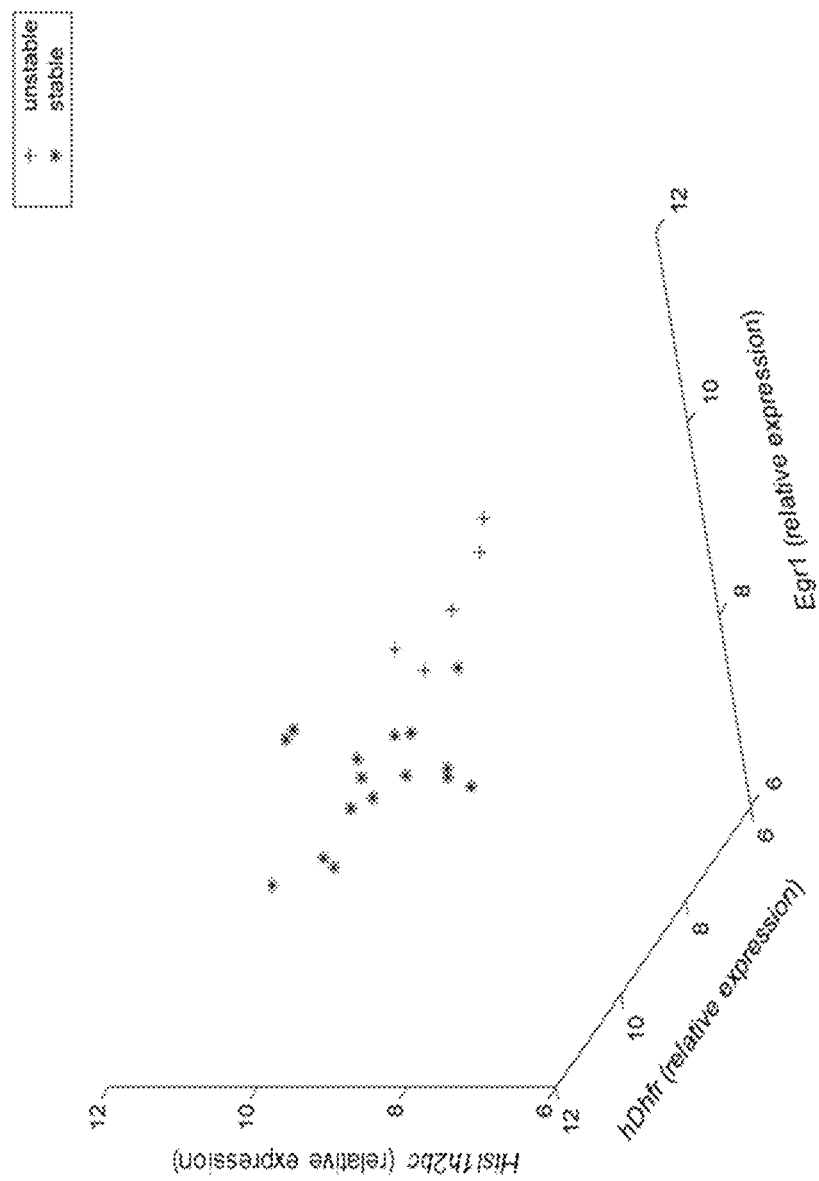
Figure 8:
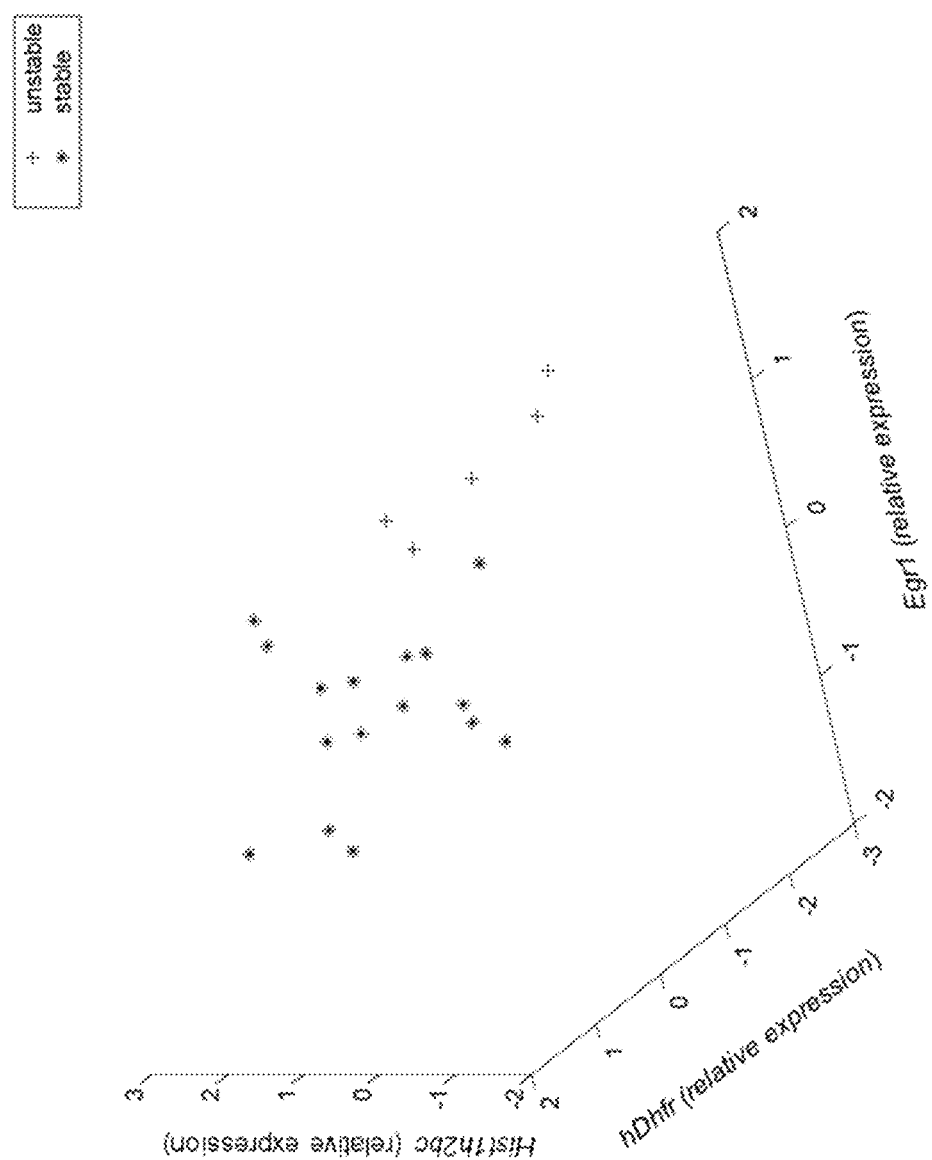
FIG. 8 is a three-dimensional representation corresponding to the data of FIG. 6, the data being plotted for three genes hDhfr (hamster Dhfr), Egr1, Hist1h2bc. The mean of relative expression values for each gene were calculated and then the mean was subtracted from the gene expression from each sample.

The same 3 genes (Egr1, hDhfr, Hist1h2bc) were used for describing the properties of stable and unstable clones in three-dimension space, originating at the end of 10-week long genetic stability study. Furthermore, a clear separation in the three-dimension space among stable and unstable clones, originating at the end of 10-week long study, was achieved (FIGS. 6 and 8). Further, a clear separation among stable and unstable clones in a three-dimension space is observed at the beginning and at the end of the long term cultivation. Based on the combined expression values of these 3 marker genes, or any other combination of genes in FIG. 4, the unstable clones can be excluded in early phases of cell line development. This way a lot of labour intensive work and especially time can be saved in bioprocess development.

Example 7: Presence of MTX

As mentioned above the expression profile of 14 top differentially expressed genes between stable and unstable clones (log $FC_{abs}$>0.8) was verified using RT-qPCR. Among these, Fgfr2, BX842664.2/Hist1h3c, E130203b14Rik, Cspg4, Mmp10 and Ptpre were identified as particularly unaffected by presence of MTX.

Figure 9:
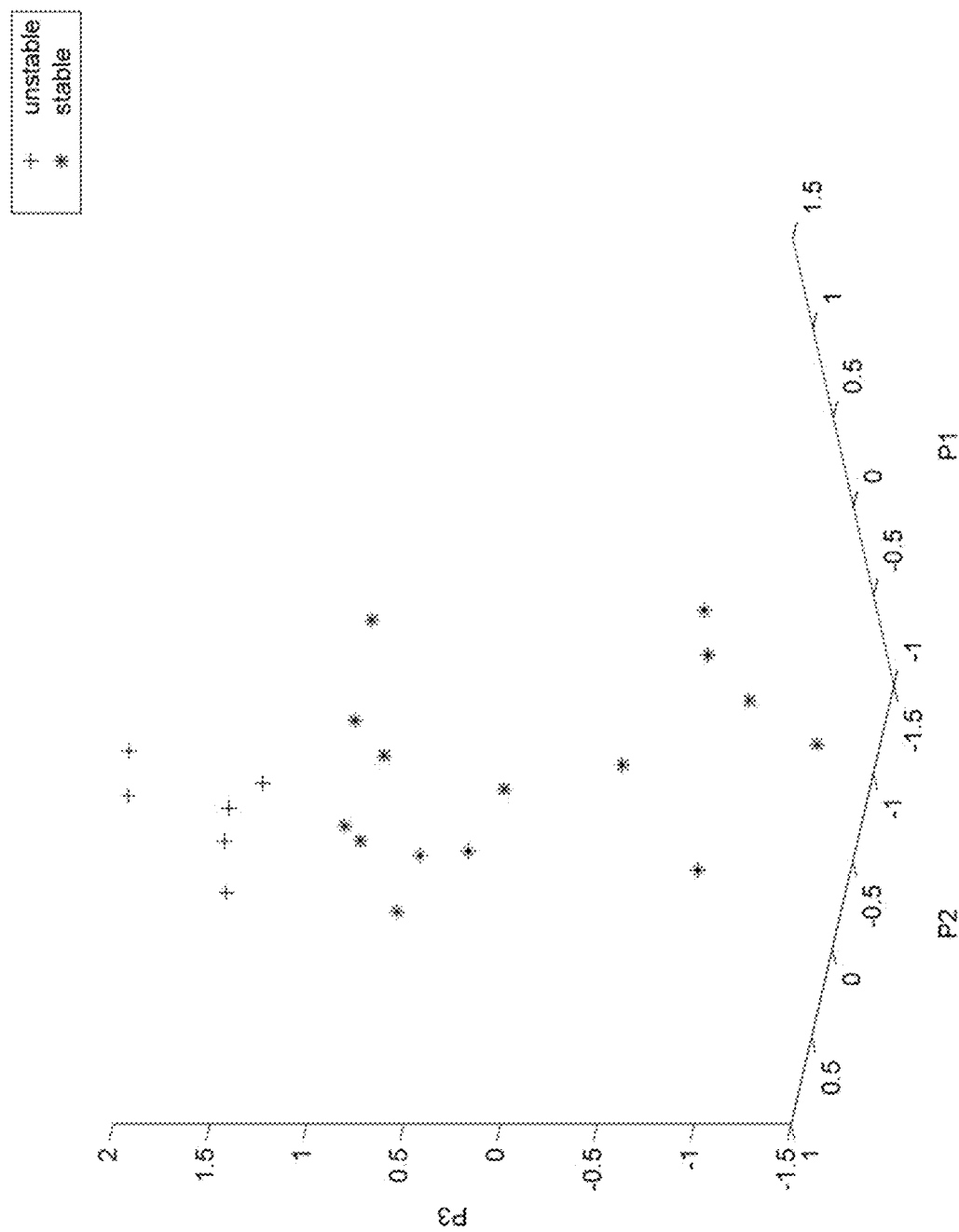
FIG. 9 is a three-dimensional representation based on principal component analysis. The properties of the clones (originating from the beginning of the study) are described by the first three principal components (P1, P2, and P3) of the expression of Fgfr2, BX842664.2/Hist1h3c, E130203b14Rik, Cspg4 and Ptpre gene.

Principal component analysis [J. Edward Jackson, A User's Guide to Principal Components, 2003, John Wiley & Sons, Inc. Hoboken, N.J., USA] was performed on the expression data (RT-qPCR data) of the five most specifically expressed gene and the three most significant principal components were presented in the 3D figure. The 15 stable and 6 unstable samples originating from beginning of the stability study are shown in FIG. 9. The five most significantly differentially expressed genes between stable and unstable samples were selected. Principal component analysis of the five genes' expressions showed that more than 92% of the total variability of the gene expression data can be explained with the first three principal components. When the first three principal components are presented in the 3D graph (FIG. 9) a clear separation of the stable vs. unstable samples can be achieved. The classification with the k-nearest neighbour algorithm also confirmed the separation of the two groups. The algorithm clusters the data into a number of predefined clusters, however, no information on cluster membership is provided in advance. By combining the expression patterns of E130203B14Rik, BX842664.2/Hist1h3c, Ptpre, Cspg4, and Fgfr2 (Mmp10 gene excluded here from the data) using principal component analysis a clear separation of the stable and unstable samples can be achieved by observing just the first three most significant principal components (FIG. 9). Based on this analysis the unstable clones can be excluded already in the early stage of the cell line development.

Example 8: CRISPR/CAS9 Experiment

CRISPR (Clustered Regularly Interspaced Short Palindromic Repeats) is used in the art as RNA guided genome editing tool. The CRISPR system was discovered in bacteria where it acts as bacterial immune system to defend against invading viruses. The technology has been routinely used in the art to functionally inactivate genes in cells, to overexpress genes of interest in cells or for exchanging/swapping genes in cells.

The purpose of the experiment will be to further verify the importance of the expression level of the genes identified previously as being relevant for stable recombinant protein production. In this experiment, those genes will be analysed first which have been shown to be downregulated in high producing clones. This will be done by using the CRISPR/CAS9 genome editing tool targeting one or more, preferably all 6 of the identified marker genes: Egr1, E130203B14Rik, Cspg4, C1qtnf1, Foxp2, and Ptpre.

Clones (in particular CHO cell derives cell clones) already producing recombinant protein will be co-transfected with a vector containing puromycin resistance and the specific nucleotide sequence targeting marker gene (CRISPR). 3 or more clones (previously identified as high producing clones) will be transfected with the "CRISPR vector". In parallel a control will be used for each clone, the control lacking transfection with the "CRISPR vector". After transfection puromycin will be used for selection purpose and afterwards 10-day batch cultivation at three timepoints will be performed. Then the titre of recombinant protein will be measured.

The inventors expect, that for all genes tested, the (stable) productivity will be better after treatment with "CRISPR vectors" targeting the individual genes as compared to the control (i.e. w/o any CRISPR vector). In other words, the (stable) productivity will be even further improved by additional silencing of genes identified in the present invention as important for stable recombinant protein production when downregulated.

It is also conceivable to use the CRISPR tool in a later experiment for studying in more detail the marker genes shown to be upregulated in high producing clones, i.e. Hist1h2bc, BX842664.2/Hist1h3c, Dhfr, AC115880.11, Fgfr2, Hist1h2bc, Mmp10, Vsnl1 and CU459186.17.

The invention claimed is:

1. Method for selecting a suitable candidate cell clone for recombinant protein expression, the method comprising the steps of:
   a) determining for at least two cell clones the RNA expression level of a marker gene selected from the group consisting of:
      histone cluster 1, H2bc Gene (Hist1h2bc), early growth response 1 gene (Egr1), Mouse DNA sequence from clone RP23-293P3 on chromosome 2/histone cluster 1, H3c (BX842664.2/Hist1h3c), dihydrofolate reductase (Dhfr), fibroblast growth factor receptor 2 (Fgfr2), AC115880.11, matrix metallopeptidase 10 (Mmp10), CU459186.17, E130203B14Rik, chondroitin sulfate proteoglycan 4 gene (Cspg4), C1q and tumor necrosis factor related protein 1 (C1qtnf1), forkhead box P2 gene (Foxp2), visinin-like 1 (Vsnl1), and protein tyrosine phosphatase, receptor type E (Ptpre), and
   b) selecting out of said at least two cell clones a cell clone for further expansion, whose RNA expression level of said gene is with respect to the expression level of said same gene in at least one other clone tested in step a):
      i) upregulated, if the gene is a gene selected from the group of genes consisting of: Hist1h2bc, BX842664.2/Hist1h3c, Dhfr, AC115880.11, Fgfr2, Mmp10, Vsnl1 and CU459186.17, or
      ii) downregulated, if the gene is a gene selected from the group of genes consisting of: Egr1, E130203B14Rik, Cspg4, C1qtnf1, Foxp2, and Ptpre.

2. The method according to claim 1, wherein the at least two cell clones express a recombinant protein.

3. The method according to claim 1, wherein the expression level of more than one gene selected from the group consisting of:
   Hist1h2bc, Egr1, BX842664.2/Hist1h3c, Dhfr, Fgfr2, AC115880.11, Mmp10, CU459186.17, E130203B14Rik, Cspg4, C1qtnf1, Foxp2, Vsnl1 and Ptpre,
   is determined and wherein a clone is selected for further expansion, whose expression level taken together for said genes is higher than the expression level of said genes taken together in at least one other clone tested in step a).

4. The method according to claim 1, wherein the expression level of a gene selected from the group consisting of: Egr1, BX842664.2/Hist1h3c, Dhfr, Fgfr2, AC115880.11, Hist1h2bc, Mmp10, CU459186.17, E130203B14Rik, Cspg4, C1qtnf1, Foxp2, and Ptpre, is determined.

5. The method according to claim 1, wherein the expression level of at least one gene selected from the group consisting of Hist1h2bc, Egr1, and Dhfr is determined in step a).

6. The method according to claim 1, wherein the expression level of at least one gene selected from the group consisting of Fgfr2, BX842664.2/Hist1h3c, E130203b14Rik, Cspg4, Mmp10 or Ptpre is determined in step a).

7. The method according to claim 6, wherein at least three genes are selected from said group.

8. The method according to claim 7, wherein a clone is selected for further expansion, whose expression level for said at least three genes is taken together superior to the expression level of said genes taken together in at least one other clone tested in step a).

9. The method according to claim 1, wherein a clone is selected in step b) for further expansion, whose expression level for said gene or expression levels taken together for said genes, respectively, is higher than the mean expression level for said gene or mean expression level taken together for said genes, respectively, as determined for two or more other clones tested in step a).

10. The method according to claim 1, wherein the clone is selected in step b) on basis of an identical or higher expression level for said gene or expression level taken together for said genes, respectively, as compared to at least one second clone tested in step a),
    wherein, if only one gene is tested in step a), said at least one second clone exhibits an expression level of said gene, which is with respect to the expression level of said same gene in at least one other clone tested in step a):
       i) upregulated, if the gene is a gene selected from the group of genes consisting of: Hist1h2bc, BX842664.2/Hist1h3c, Dhfr, AC115880.11, Fgfr2, Mmp10, Vsnl1 and CU459186.17, or
       ii) downregulated, if the gene is a gene selected from the group of genes consisting of: Egr1, E130203B14Rik, Cspg4, C1qtnf1, Foxp2, and Ptpre, or
    wherein, if more than one gene is tested in step a), said at least one second clone exhibits an expression level taken together for said genes which is higher than the expression level of said genes taken together in at least one further clone tested in step a).

11. The method according to claim 1, wherein the method further comprises the step of:
    c) expanding said selected cell clone.

12. The method according to claim 1, wherein the cell clones are Chinese hamster ovary (CHO) cell clones.

13. The method according to claim 1, wherein determining the expression level in step a) involves quantitative RT-PCR.

14. The method according to claim 1, wherein the expression level of three genes selected from the group consisting of:
    Hist1h2bc, Egr1, BX842664.2/Hist1h3c, Dhfr, Fgfr2, AC115880.11, Mmp10, CU459186.17, E130203B14Rik, Cspg4, C1qtnf1, Foxp2, Vsnl1 and Ptpre,
    is determined and wherein the selection in step b) is made by using a three-dimensional representation of the results.

* * * * *